(12) United States Patent
Shah

(10) Patent No.: US 12,174,121 B2
(45) Date of Patent: Dec. 24, 2024

(54) APPLICATION OF RAMAN SPECTROSCOPY FOR THE MANUFACTURE OF INHALATION POWDERS

(71) Applicant: NORTON (WATERFORD) LIMITED, Waterford (IE)

(72) Inventor: Hardik Kirtikumar Shah, Waterford (IE)

(73) Assignee: NORTON (WATERFORD) LIMITED, Waterford (IE)

( * ) Notice: Subject to any disclaimer, the term of this patent is extended or adjusted under 35 U.S.C. 154(b) by 213 days.

(21) Appl. No.: 17/745,686

(22) Filed: May 16, 2022

(65) Prior Publication Data

US 2022/0276173 A1 Sep. 1, 2022

Related U.S. Application Data

(63) Continuation of application No. 17/380,535, filed on Jul. 20, 2021, now Pat. No. 11,366,064, which is a
(Continued)

(51) Int. Cl.
*G01N 21/65* (2006.01)
*A61K 9/00* (2006.01)
(Continued)

(52) U.S. Cl.
CPC .......... *G01N 21/65* (2013.01); *A61K 9/0075* (2013.01); *A61K 31/138* (2013.01); *A61K 31/567* (2013.01); *A61K 45/06* (2013.01); *G01J 3/44* (2013.01); *G01N 21/85* (2013.01); *G01N 2021/8592* (2013.01)

(58) Field of Classification Search
CPC ............. G01N 21/65; G01N 21/85; G01N 2021/8592; G01N 21/9508; A61K 9/0075; A61K 31/138; A61K 31/567; A61K 45/06; A61K 9/141; G01J 3/44; B01F 35/213
See application file for complete search history.

(56) References Cited

U.S. PATENT DOCUMENTS 8,198,354 B2 * 6/2012 Miller .................... A61P 29/00
528/495
8,778,402 B2 7/2014 Monari et al.
(Continued)

FOREIGN PATENT DOCUMENTS

AU 2011296343 B2 * 12/2015 .......... A61K 31/137
CN 102149438 8/2011
(Continued)

OTHER PUBLICATIONS

Allan, P. et al.: "In situ monitoring of powder blending by non-invasive Raman spectrometry with wide area illumination", vol. 76, Mar. 2013, pp. 28-35.
(Continued)

*Primary Examiner* — Mohamed K Amara
(74) *Attorney, Agent, or Firm* — Pillsbury Winthrop Shaw Pittman, LLP

(57) ABSTRACT

The present invention generally relates to improved methods for the manufacture of inhalation powders. More particularly, aspects of the disclosure relate to methods for in-line monitoring of powder blending by Raman spectroscopy.

23 Claims, 18 Drawing Sheets

Related U.S. Application Data continuation of application No. 17/266,884, filed as application No. PCT/IB2019/056737 on Aug. 7, 2019, now Pat. No. 11,774,363.

(60) Provisional application No. 62/715,463, filed on Aug. 7, 2018.

(51) Int. Cl.
| | | |
|---|---|---|
| *A61K 31/138* | (2006.01) | |
| *A61K 31/567* | (2006.01) | |
| *A61K 45/06* | (2006.01) | |
| *G01J 3/44* | (2006.01) | |
| *G01N 21/85* | (2006.01) | |

(56) References Cited

U.S. PATENT DOCUMENTS

| | | | |
|---|---|---|---|
| 9,072,664 B2* | 7/2015 | Stein | A61K 9/0075 |
| 9,439,862 B2 | 9/2016 | Weers et al. | |
| 11,173,115 B2* | 11/2021 | Sung | A61P 11/00 |
| 2005/0121027 A1* | 6/2005 | Nilsson | A61K 9/008 128/200.23 |
| 2008/0025966 A1* | 1/2008 | Currie | A61P 1/12 424/94.64 |
| 2009/0291146 A1 | 11/2009 | Roche et al. | |
| 2010/0189780 A1* | 7/2010 | Walz | A61M 11/003 53/410 |
| 2011/0139152 A1 | 6/2011 | Morton et al. | |
| 2012/0071449 A1 | 3/2012 | Kamlag et al. | |
| 2012/0309729 A1* | 12/2012 | Ruecroft | B01D 1/18 540/71 |
| 2013/0177651 A1 | 7/2013 | Nyambura | |
| 2013/0338606 A1* | 12/2013 | Conzone | A61M 5/31513 604/230 |
| 2014/0065219 A1 | 3/2014 | Bosch et al. | |
| 2014/0336159 A1* | 11/2014 | Clarke | A61K 45/06 514/557 |
| 2015/0157566 A1* | 6/2015 | Kim | A61K 47/26 424/499 |
| 2016/0271345 A1* | 9/2016 | Blair | A61M 15/0026 |
| 2017/0239177 A1* | 8/2017 | Dalvi | A61P 11/06 |
| 2020/0261667 A1* | 8/2020 | DeHaan | A61M 15/0001 |
| 2021/0293715 A1 | 9/2021 | Shah | |
| 2022/0047610 A1 | 2/2022 | O'Neill et al. | |

FOREIGN PATENT DOCUMENTS

| | | | |
|---|---|---|---|
| CN | 102946868 | 2/2013 | |
| KR | 20170118975 | 10/2017 | |
| WO | WO-2005044186 A2 * | 5/2005 | A61K 9/0075 |
| WO | 2011/069197 | 6/2011 | |
| WO | 2011120779 | 10/2011 | |
| WO | 2013/075086 | 5/2013 | |

OTHER PUBLICATIONS

Debeer, T. et al.: "Near infrared and Raman spectroscopy for the in-process monitoring of pharmaceutical production processes", International Journal of Pharmaceutics, vol. 417, Sep. 2011, pp. 32-47.

Wang, H. et al.: "Macro-Raman spectroscopy for bulk composition and homogeneity analysis of multi-component pharmaceutical powders", Journal of Pharmaceutical and Biomedical Analysis, vol. 141, Apr. 23, 2017, pp. 180-191.

Riolo, D. et al.: "Raman spectroscopy as a PAT for pharmaceutical blending: Advantages and disadvantages", Journal of Pharmaceutical and Biomedical Analysis, vol. 149, Feb. 2018, pp. 329-334.

International Search Report and Written Opinion issued in corresponding PCT Patent Application No. PCT/IB2019/056737, dated Nov. 27, 2019.

International Preliminary Report on Patentability and Written Opinion issued in corresponding International Application No. PCT/IB2019/056737 on Feb. 9, 2021.

Albuterol as a Beta2 Agonists, downloaded from: https://www.aaaai.org/Tools-for-the-Public/Allergy,-Asthma-Immunology-Glossary/Beta2-agonists-Defined.

Office Action dated Jan. 26, 2022, issued in U.S. Appl. No. 17/410,774, filed Aug. 24, 2021, pp. 1-12.

El-Gendy et al., Nanoparticle agglomerates of fluticasone propionate in combination with albuterol sulfate as dry powder aerosols; Elsevier; European Journal of Pharmaceutical Sciences, 44 (2011), 522-533.

Office Action issued in corresponding European Patent Application No. 21181874.5, dated May 31, 2023.

M. D. Jones et al., "The relationship between drug concentration, mixing time, blending order and ternary dry powder inhalation performance", International Journal of Pharmaceutics, vol. 391, pp. 139-147 (2010).

Highlights of Prescribing Information, "Advair HFA", Food and Drug Administration, pp. 1-54 (Jul. 2023).

I. Axelsson et al., "Effets of inhaled corticosteroids on growth in children with persistent asthma: Impact of drug molecules and delivery devices—An overview of Cochrane reviews", ScienceDirect, Paediatric Respiratory Review, 32, pp. 28-29 (2019).

Highlights of Prescribing Information, "Flovent Diskus", Food and Drug Administration, pp. 1-33 (Aug. 2023).

D. B. Allen, "Inhaled Corticosteroids and Endocrine Effects in Childhood", Endocrinol. Metab. Clin. N. Am., 49. pp. 651-665 (2020).

1. Axelsson et al., Inhaled corticosteroids in children with persistent asthma: effects of different drugs and delivery devices on growth, Cochrane Database of Systematic Reviews, Issue 6, pp. 1-38 (2019).

"The Changing Role of Inhaled Corticosteroids in Asthma Management", NIH Publication, No. 20-HL-8148, pp. 1-3 (Dec. 2020).

M. Blaiss et al., "Safety of ciclesonide in children with asthma: A review of randomized controlled trials", Allergy and Asthma Proceedings, vol. 42, No. 6, pp. 471-480 (Nov. 2021).

U. Nalin et al., "Single inhaler maintenance and reliever therapy in pediatric asthma", Current Opinion, Review, vol. 19, No. 2 pp. 1-7 (Apr. 2019).

Highlights of Prescribing Information, Symbicort®, AstraZeneca, pp. 1-18 (Dec. 2017).

The Pharmacological Basis of Therapeutics, "Glucocorticoids", Pharma Therapy of Asthma, Chapter 27, pp. 721-722 (2006).

* cited by examiner

APPLICATION OF RAMAN SPECTROSCOPY FOR THE MANUFACTURE OF INHALATION POWDERS

CROSS-REFERENCE TO RELATED APPLICATIONS

This application is a continuation of U.S. application Ser. No. 17/380,535, filed Jul. 20, 2021, now allowed, which is a continuation of U.S. application Ser. No. 17,266,884, filed on Feb. 8, 2021, which is a National Phase of International Patent Application No. PCT/IB2019/056737, filed Aug. 7, 2019, which claims priority to U.S. Provisional Patent Application No. 62/715,463, filed Aug. 7, 2018, each of which is hereby expressly incorporated by reference in its entirety.

FIELD

The present invention generally relates to improved methods for the manufacture of inhalation powders. More particularly, aspects of the disclosure relate to in-line Raman spectroscopic methods for monitoring and controlling the blending of a dry powder for inhalation.

BACKGROUND

Inhalation therapy is currently the best option for lung diseases such as asthma, cystic fibrosis, and chronic obstructive pulmonary disease (COPD). Pulmonary delivery allows the use of smaller drug doses and reduced systemic side effects. Moreover, pulmonary delivery is attractive as a route for systemic administration due to fast absorption by the massive surface area of the alveolar region, the abundant vasculature and thin air-blood barrier, and the avoidance of first pass metabolism. (Ibrahim et al., Medical Devices: Evidence and Research, 2015, 8: 131-139).

Two widely used systems for the administration of drugs to the airways are dry powder inhalers (DPIs) comprising micronized drug particles as dry powder usually admixed with coarser excipient particles of pharmacologically inert materials such as lactose, and pressurized metered-dose inhalers (pMDIs) comprising a suspension of micronized drug particles in a propellant gas. DPI formulations have greater chemical stability than liquid formulations, but manufacturing powders with the appropriate characteristics for easy aerosolization and alveolar delivery is more complicated. The drug particles to be delivered must be sufficiently small so that the particles can be inhaled and penetrate into the deep lung. The aerodynamic diameter of the particles primarily influences this behavior, since deposition in the respiratory tract is controlled by a particle's aerodynamic size rather than its physical or geometric shape. Lung deposition improves substantially for particles less than 5 microns in aerodynamic diameter and decreases substantially for particles with effective aerodynamic diameters of greater than 5 microns. A drug particle size between 1 microns and 5 microns is needed for entry into the deep lung by inhalation; drug particles of 1-2 microns are most suitable for reaching the small airways, an important target for the treatment of asthma and chronic obstructive pulmonary disease (COPD).

DPI drug formulations may either be a fine powder of drug blended with large carrier particles to prevent aggregation and increase powder flow prior to aerosolization, or may consist of drug alone. In all cases, the powder formulations travel along the airways to deposit in the targeted areas of the lung, and then dissolve to exert their pharmacological effect or are absorbed to reach systemic targets. Powder blends for DPIs typically consist of micronized drug particles blended with an inactive excipient (e.g., lactose, mannitol, trehalose, sucrose, sorbitol, glucose) of larger particle size. These components are usually blended together to form an "interactive mixture" wherein the finer drug particles are adhered to the surface of the carrier particles. Unoptimized powder blends can exhibit interparticulate cohesive forces that cause powder aggregates, making drug dispersion very difficult.

Manufacturing powder blends containing micronized APIs is a challenging process. Micronized drugs, especially drug particles having a diameter within the range of from about 1-5 microns, have a high surface energy and substantial adhesive and cohesive properties. Some APIs used in dry powder inhalation products are particularly challenging to homogenize. For example, the cohesive nature of salmeterol xinafoate is well documented. It is possible to improve homogeneity of salmeterol xinafoate by increasing the blending energy, however, this may adversely affect the aerodynamic particle size distribution.

The traditional approach within the pharmaceutical industry for assessing drug content uniformity of a blend involves sampling of the blend using a sample thief followed by off-line analysis using an HPLC method. Unfortunately, sample thieves are intrusive devices that are prone to sampling error. A sample thief is a metal cylinder with one of more recessed cavities that can be opened and closed by twisting a handle; it is commonly used to collect samples from stationary material in a blender. An operator inserts the thief into the material bed, opens the cavities allowing material to flow in, then closes the cavities and removes the thief with sample material inside. The act of sampling violates the first golden rule of sampling which is to sample material when it is in motion. Inserting the sample thief into stationary material disturbs the powder bed and can cause sampling irregularities. Also some ingredients may not flow well into the thief cavities or may adhere to the thief itself. (Eric Maynard, Powder and Bulk Engineering, January 2015, "Five fundamentals for effective blend sampling")

On-line methods allow sampling while the blend is in motion and generate real time blend uniformity analysis. Analytical methodology used on-line is consistent with FDA Guidelines for Manufacturers, which encourages the development of a quality by design approach that combines a higher level of process understanding with real-time monitoring and control manufacturing (FDA, Guidance for Industry: PAT-A Framework for Innovative Pharmaceutical Development, Manufacturing, and Quality Assurance, September 2004).

Both Near-infrared (NIR) and Raman spectroscopy have been used for the in-process monitoring of many pharmaceutical production processes, such as powder blending, granulation, drying, tablet manufacture, coating, pelletization, freeze-drying, and hot melt extrusion. (De Beer et al., International Journal of Pharmaceutics, 2011, 417: 32-47). NIR and Raman spectroscopy are fast, precise, noninvasive, and nondestructive techniques that require little or no sample preparation and provide complementary information about molecular structure. These techniques measure vibrational energy levels associated with the chemical bonds in a sample, and generate a spectrum that is unique, like a molecular fingerprint. The most widely used and documented process analytical technology (PAT) tool is NIR spectroscopy.

In Near-infrared spectroscopy, the sample is irradiated with polychromatic light in the NIR region of the electromagnetic spectrum (i.e., 4000-12500 cm$^{-1}$). A photon of light is absorbed when the energy of the absorbed light matches the energy required for a particular bond to vibrate within the sample. In order for a molecule to be infrared active, the molecular dipole moment must change during the vibration. Absorbances observed in NIR spectroscopy result mainly from C—H, O—H, N—H and S—H functional groups. NIR absorption spectra are often complex and normally possess broad overlapping NIR absorption bands that require special mathematical procedures for data analysis.

In Raman spectroscopy, the sample is irradiated with monochromatic light and the photons are either elastically scattered (ca. 99.999%) or inelastically scattered (ca. 0.001%). The elastically scattered light, known as Rayleigh scatter, has the same energy as the incident laser light and is not useful for purposes of molecular characterization. The inelastically scattered light, known as Raman scatter, has either lost energy (Stokes frequency) or gained energy (Anti-Stokes frequency) during this interaction. The emitted photons contain information about the molecular structure of the sample. Since Raman scattering is very weak, the intensity of light from the Rayleigh scattering may greatly exceed the intensity of the useful Raman signal in close proximity to the laser wavelength.

In order for a molecule to be Raman active, there must be a change in polarizability when the molecule vibrates (i.e., a change in the shape, size or orientation of the electron cloud that surrounds the molecule). Bonds that are relatively nonpolar, such as C—C, C—H undergo large changes in polarizability during a vibration, particularly moieties with distributed electron clouds (e.g., C=C). In addition to intramolecular vibrations, crystal lattice vibrations may also be Raman active. A crystalline material will typically yield a Raman spectrum with very sharp, intense peaks whilst an amorphous material will show broader, less intense peaks. A significant challenge in the application of Raman spectroscopy for many organic and biological samples is background fluorescence, which can be orders of magnitude stronger than Raman scattering.

As compared to Near-infrared spectroscopy, the use of Raman spectroscopy for pharmaceutical blending has been less frequently described in the literature (Pharmaceutical Blending and Mixing, 2015, John Wiley & Sons, Chapter 15, Nicolas Abatzoglou, "Process Analytical Technology for Blending"). In 2005, Hausman et al. disclosed the use of in-line Raman spectroscopy for qualitative analysis of low dose blend uniformity in a 1% azimilide dihydrochloride powder blend formulated with spray-dried lactose, crospovidone, and magnesium stearate (Hausman et al., International Journal of Pharmaceutics, 2005, 298: 80-90). Throughout the blending process, the blender content was monitored by Raman spectroscopy using a fiber optic probe inserted into the V-blender through the I-bar port. Hausman does not teach, however, quantitative determination of drug substances, blend homogeneity of micronized drug substances, chemometric determination of two drug substances in the same blend, or homogeneity of blend during a high shear mixing process.

Also in 2005, Tummala et al. disclosed a method of monitoring the blending of a mixture containing at least two blendable components having different peak spectra employing, for example, light-induced fluorescence spectroscopy, NIR spectroscopy, and Raman spectroscopy. (Tummala et al., US 2005/0032235). In Example 1, Raman spectroscopy using a non-contact probe was used for qualitative analysis of a powder blend containing four components, including the active ingredient gatifloxacin and excipients xylitol, sucrose, and aspartame. Tummala does not teach, however, quantitative determination of drug substances, blend homogeneity of micronized drug substances, chemometric determination of two drug substances in the same blend, or homogeneity of blend during a high shear mixing process.

Despite the efficiencies it may offer, the use of in-line Raman spectroscopic methods for qualitative and quantitative analysis of powder blending processes is not common in the pharmaceutical industry. A robust, reliable Raman spectroscopy method for in-line monitoring of a blending process suitable for the commercial manufacture of dry powder inhalation formulations would be highly desirable. It would be further desirable to provide a method applicable to dry powders containing two or more active pharmaceutical ingredients, wherein each active ingredient has a concentration of <1.0 wt. %. Further still, the method should be applicable to dry powders comprising micronized active pharmaceutical ingredients.

SUMMARY OF THE INVENTION

An aspect of the disclosure is to provide an in-line Raman spectroscopic method for monitoring and controlling the blending of a dry powder for inhalation, wherein the dry powder comprises at least two active pharmaceutical ingredients (APIs) and an excipient as components. The method may include (i) providing a Raman spectroscopic system comprising a Raman analyzer, at least one non-contact probe; and a processing device; (ii) blending the dry powder for inhalation; (iii) collecting Raman spectroscopic data during the blending process; (iv) transmitting the Raman spectroscopic data to a processing device; (v) analyzing the Raman spectroscopic data to determine blend homogeneity; and (vi) optionally, modifying the blending process in order to meet criteria for blend uniformity of the dry powder. In a preferred embodiment, each component in the dry powder has a unique Raman emission spectrum which does not significantly overlap any of the Raman emission spectra of the other components.

The methods disclosed herein can be used as a process analytical technology (PAT) tool for the end point control of a powder blending process. Further, the inventive methods can be used for quantitative analysis of content uniformity. Other objects and features of the embodiments will be apparent to those having ordinary skill in the art upon review of this disclosure.

DETAILED DESCRIPTION

Figure 1A:
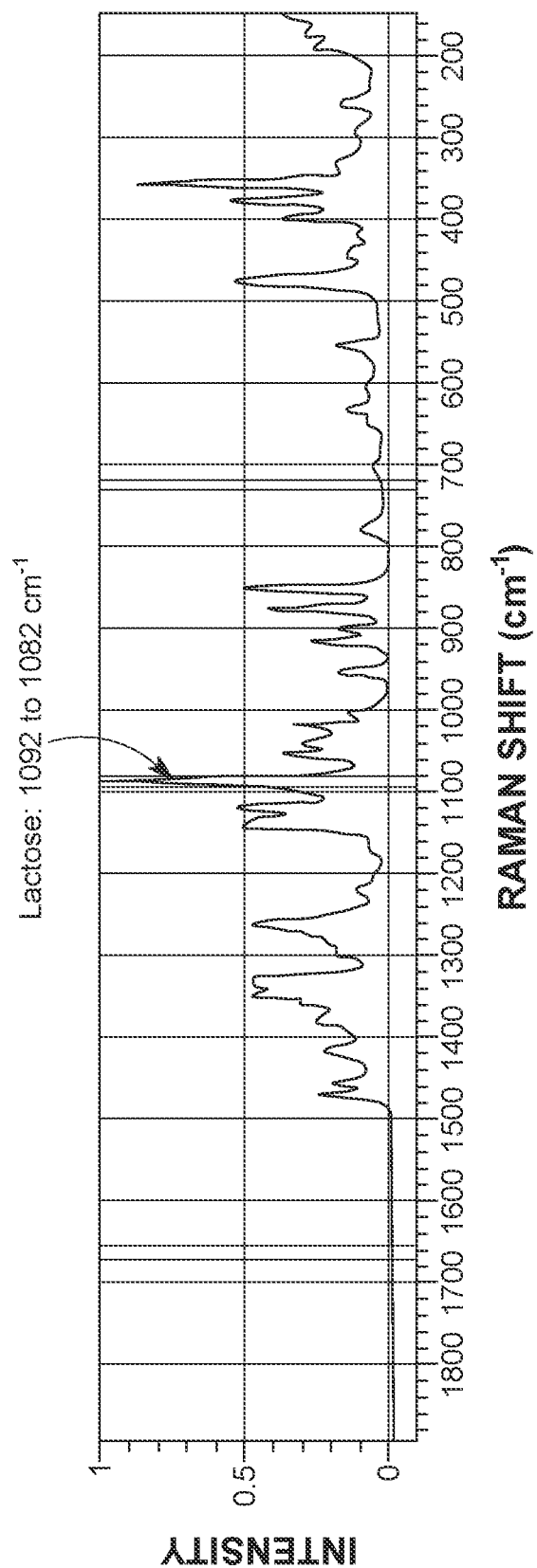
FIGS. 1A-1C show the individual Raman spectrum for each component in the Fluticasone Propionate-Salmeterol Xinafoate blend, with assignment of characteristic peaks, in accordance with one or more embodiments.

When describing features of aspects or preferred embodiment(s) thereof, the articles "a", "an", "the", and "said" are intended to mean that there are one or more of the elements. The terms "comprising", "including" and "having" are intended to be inclusive and mean that there are additional elements other than the listed elements.

The expressions "active pharmaceutical ingredient" or "active ingredient" or "API" or "active agent" as used herein means any component that is intended to furnish activity or other direct effect in the diagnosis, cure, mitigation, treatment, or prevention of disease, or to affect the structure or any function of the body of man or other animals. The term includes those components that may undergo chemical change in the manufacture of the drug product and be present in the drug product in a modified form intended to furnish the specified activity or effect.

The term "batch" as used herein means a specific quantity of a product that is intended to have uniform character and quality, within specified limits, and is produced according to a single manufacturing order during a same cycle of manufacture. Batch refers to the quantity of material and does not specify a mode of manufacture.

The term "batch process" as used herein means a process wherein all materials are charged before the start of processing and all products are discharged at the end of processing.

The term "carrier agent" or "carrier particle" as used herein, is an excipient or inert ingredient to which particles of the drug or active ingredient adhere when an interactive mixture is formed. Micronized active particles, because of the electrostatic or Van der Waals interactions, mainly adhere to the surface of such carrier particles whilst in the inhaler device, but during inhalation, a redispersion of the drug particles from the surface of the carrier particles occurs allowing the drug particles to reach the absorption site in the lungs. Carrier particles for use in dry powder inhalers are well known in the art and described in, for example, GB 1,242,211, GB 1,381,872, WO 95/11666, and U.S. Pat. No. 7,132,155, the disclosures of which are incorporated by reference herein in their entirety.

The term "chemometric analysis" as used herein refers to the use of mathematical and statistical methods to improve the understanding of chemical information and to correlate quality parameters or physical properties to analytical instrument data.

The term "continuous process" as used herein denotes a process composed of integrated (physically connected) continuous unit operations with zero or minimal hold volume in between. A "semi-continuous" process is a continuous process operated for a discrete time period.

The term "dry powder" as used herein refers to a powder composition that typically contains less than about 20% moisture, preferably less than 10% moisture, and more preferably contains less than about 5-6% moisture, depending upon the particular formulation.

The term "excipient" (also "inactive ingredient") as used herein means any component other than an active ingredient.

The term "pharmaceutically acceptable" as used herein refers to those compounds, materials, compositions, and/or dosage forms which are, within the scope of sound medical judgement, suitable for use in contact with the tissues of human beings and animals without excessive toxicity, irritation, allergic response or other problem or complication, commensurate with a reasonable benefit/risk ratio.

The term "pharmaceutically acceptable salt" as used herein refers to the relatively non-toxic, inorganic and organic, acid or base addition salts of compounds of disclosed herein. Representative salts include, for example, those listed in Berge et al., "Pharmaceutical Salts," J. Pharm Sci, 1977, 66: 1-19. Pharmaceutically acceptable acid addition salts include, but are not limited to, those formed from hydrochloric, hydrobromic, sulfuric, citric, tartaric, phosphoric, lactic, pyruvic, acetic, trifluoroacetic, succinic, oxalic, fumaric, maleic, oxaloacetic, methanesulphonic, ethanesulphonic, p-toluenesulphonic, benzenesulphonic, isethionic, and naphthalenecarboxylic, such as 1-hydroxy-2-naphthalenecarboxylic (i.e., xinafoic) acids.

The term "Raman spectroscopy" as used herein refers to a spectroscopic technique that probes the specific molecular content of a sample by collecting in-elastically scattered light.

"Aerodynamic diameter" denotes the diameter of a sphere of unit density which behaves aerodynamically as the particle of the test substance. It is used to compare particles of different sizes, shapes and densities and to predict where in the respiratory tract such particles may be deposited. The term is used in contrast to volume equivalent, optical, measured or geometric diameters which are representations of actual diameters which in themselves cannot be related to deposition within the respiratory tract. The aerodynamic diameter, $d_{aer}$, can be calculated from the equation:

$$d_{aer} = d_g \sqrt{\rho_{tap}}$$

where $d_g$ is the geometric diameter, for example the mass median geometric diameter (MMGD), and $\rho$ is the powder density. See, for example, U.S. Pat. No. 9,539,211, the disclosure of which is incorporated herein by reference in its entirety.

"Blend uniformity" (BU) refers in general to a measure of the uniformity of a blend of powder. The FDA published a draft guidance document for analyzing blend uniformity in August 1999 (FDA, "Guidance for Industry; ANDAs: Blend Uniformity Analysis," Aug. 3, 1999, available at https://www.fda.gov/OHRMS/DOCKETS/98fr/992635gd.pdf).

The draft guidance document states that an "acceptable blend uniformity," which is defined herein with the same definition, is one in which 90.0 to 110.0 percent of the expected quantity of the active ingredient is recovered with a relative standard deviation (RSD) of no more than 5.0%. Standards for assessing blend uniformity must comply with regulations set forth in, for example, 21 CFR 211.110; 211.160; 211.165, http://www.accessdata.fda.gov/scripts/cdrh/cfdocs/cfcfr/CFRsearch.cfm?CFRPart=211. A final FDA draft guidance document was published in 2003 (the "draft guidance document") that describes procedures for assessing blend uniformity and determining "acceptable blend uniformity." FDA, "Guidance for Industry; Powder Blends and Finished Dosage Units—Stratified In-Process Dosage Unit Sampling and Assessment," October 2003, available at https://www.fda.gov/ohrms/dockets/98fr/03d-0493-gd10001.pdf.

"Mass Median Aerodynamic Diameter" (MMAD) is the median of the distribution of airborne particle mass with respect to the aerodynamic diameter, e.g., as measured, for example, by cascade impaction. For instance, a MMAD of 5 microns means that 50% of the total sample mass will be present in particles having aerodynamic diameters less than 5 microns.

"Mass Median Diameter" (geometric diameter) typically refers to the median size of a population of particles by mass, where 50% of the particles are above this diameter and 50% are below this diameter, e.g., as determined by laser diffraction.

"Process Analytical Technology" has been defined by the United States Food and Drug Administration (FDA) as a mechanism to design, analyze, and control pharmaceutical manufacturing processes through the measurement of Critical Process Parameters which affect Critical Quality Attributes. (FDA, Guidance for Industry: PAT—A Framework for Innovative Pharmaceutical Development, Manufacturing, and Quality Assurance, September 2004)

"Process analyzers" are tools in the PAT framework used for real-time process monitoring and control to supply data from which relevant process and product information can be extracted. Real-time process measurement can be made: (1) at-line: measurement where the sample is removed, isolated from, and analyzed in close proximity to the process stream; (2) on-line: measurement where the sample is diverted from the manufacturing process, and may be returned to the process stream; (3) in-line: measurement where the sample is not removed from the process stream and can be invasive or noninvasive.

The vast majority of DPI products are used to treat respiratory diseases such as asthma, bronchitis, emphysema and chronic obstructive pulmonary disease (COPD). For these indications, API dosages are typically in the microgram range and require a bulking agent in the formulation in order to meter and handle the product. Thus, blending is usually a critical process in the manufacture of a dry powder for inhalation. Micronized APIs generally have an aerodynamic particle size between 1-5 microns for optimal deep lung targeting and are usually blended with an inert coarse carrier such as lactose monohydrate. However such small particles tend to have high surface energy, and are prone to agglomeration. It is necessary to balance the cohesion (API-API) and adhesion (API-carrier) forces to ensure a stable and homogeneous blend while enabling good aerosilization efficiencies.

Generally, the API has to be adhesive enough to attach to the surface of the carrier particles to form an interactive mixture that can withstand further processing, storage, and transport processes. However, the adhesive forces must be weak enough to allow for release of the API from the carrier surface upon oral inhalation. Moreover, an adequate balance of energy must be provided to the formulation during blending so that cohesive forces are overcome, enabling a homogenous drug distribution across the formulation.

Commercial formulations for the treatment of respiratory diseases may contain multiple drug components, such as fluticasone and salmeterol. This results in further complications in the particle interactions within powder systems. Yet another challenge in the development of a DPI product is the transfer of the formulation process from laboratory scale, where a low-shear mixer is commonly used, to a large scale operation, where a high shear mixer is commonly used. The different mixing principles can affect the blend properties, which in turn may affect aerosolization behavior and therapeutic efficacy.

An aspect of the disclosure provides a method for an in-line Raman spectroscopic method for monitoring and controlling the blending of a dry powder for inhalation comprising at least two active pharmaceutical ingredients (APIs) and an excipient as components. The method comprises: (i) providing a Raman spectroscopic system comprising a Raman analyzer, at least one non-contact probe; and a processing device; (ii) blending the dry powder for inhalation; (iii) collecting Raman spectroscopic data during the blending process; (iv) transmitting the Raman spectroscopic data to a processing device; (v) analyzing the Raman spectroscopic data to determine blend homogeneity; and (vi) optionally, modifying the blending process in order to meet criteria for blend uniformity of the dry powder.

The methods disclosed herein can be used as a PAT tool for the end point control of a powder blending process. Further, the inventive methods can be used for quantitative analysis of content uniformity. The methods are particularly useful for robust manufacturing processes that meet Quality by Design (QbD) principles. Moreover, the inventive methods can be used to develop efficient processes that reduce cost and time.

The inventive method can be used for monitoring and controlling the blending of a dry powder for inhalation provided the components in the dry powder are Raman active. The Raman spectra for the individual components may be obtained from a spectra library. Otherwise, the method further encompasses (i) collecting, for each component of the dry powder, an individual Raman emission spectrum; and (ii) selecting, for each component of the dry powder, a characteristic Raman peak or peaks from its individual Raman emission spectrum that can be distinguished from the peaks of all other components in the dry powder. Preferably, each component in the powder blend has a unique Raman emission spectrum that does not significantly overlap any of the spectra of the other components.

In one embodiment of the invention, the dry powder for inhalation contains the components fluticasone propionate, salmeterol xinafoate, and lactose monohydrate. The three components have distinguishable Raman peaks at 1672-1654 $cm^{-1}$, 735-724 $cm^{-1}$, and 1092-1082 $cm^{-1}$, respectively. In another embodiment of the invention, the dry powder for inhalation contains the components fluticasone propionate, albuterol sulfate, and lactose monohydrate. The three components have distinguishable Raman peaks at 1672-1654 $cm^{-1}$, 790-775 $cm^{-1}$, and 1092-1082 $cm^{-1}$, respectively.

Advantageously, a dry powder for inhalation comprises micronized particles of an active pharmaceutical ingredient and coarse particles of a physiologically acceptable carrier agent. The device used for blending the at least two APIs and carrier agent may be selected from any suitable blender or mixer used in the art. A wide variety of mixers are commonly used in the pharmaceutical industry and operate by mechanisms that include diffusion, convection, and shear. Diffusion mixers (also known as tumbling mixers) contain a closed vessel that rotates about an axis and redistribute particles by random motion. Diffusion mixers include V-blenders, double cone blenders, drum blenders, and the like. In convection blending, particles in a stationary vessel are mixed by a rotating blade, paddle, or screw. Convective mixers include ribbon blenders, screw blenders, planetary blenders, and the like. Shear mixers develop slip planes or shearing strains within a bed of material. Use of shear mixers can shorten mixing time and reduce the risk of powder agglomeration.

The device used for blending the components of the dry powder for inhalation is preferably a high shear mixer, and more preferably a mixer that uses 3-dimensional Schatz geometry linkage. Such mixers use a closed container that is set into a three dimensional movement that uses rotation, translation, and inversion according to the Schatz geometric theory, as described in, for example, Sarpale, S. A., et al., "Design and Analysis of Drive System of Schatz Geometry Shaker Mixer," IJEDR, 2016, 4(4): 512-535. For example, rotation of impeller blades at an angle to the geometric plane of the mixer can provide a shearing effect to mix the powder, and a chopper blade rotating at a vertical position can break up large agglomerates that may be present in the blend.

The blending process with a high shear mixer is generally characterized by a mixing time from about 1 minute to about 60 minutes, preferably from about 3 minutes to about 30 minutes. The impeller speed of the high shear mixer is typically from about 5 rpm to about 5000 rpm, preferably from about 50 rpm to about 2000 rpm. An example of a suitable high shear mixer is PharmaConnect® High Shear Mixer (GEA Process Engineering Inc.; Columbia MD., USA).

The order of addition of components to the blender vessel is not limited by the inventive methods and can be readily determined by the skilled artisan. For example, the carrier agent can be added, then the API, then the carrier agent, such that the API is sandwiched between two portions of the carrier agent. For low concentration blends, it may be desirable to pre-blend the components using geometric dilution, and then add the pre-blend to the blender vessel instead of adding the individual components to the blender vessel.

In one embodiment, the blending process results in the formation of an interactive mixture wherein small drug particles adhere to the surface of larger inert carrier particles, usually as a result of electrostatic or Van der Waals interactions, to provide interactive units. In practice, if a large excess of carrier particles is used, the interactive mixture may comprise interactive units and free carrier particles. It is beneficial for the adhesive interactions between drug particles and carrier particles to be reversible, so that breathing-in through the inhaler causes separation of the drug particles from the carrier particles. Specifically, interparticulate forces should be such that the drug particles adhere to the carrier particles (to aid in blending, uniformity, and allow the entrainment of drug into the inspiratory air-stream), yet also allow detachment of the micronized drug particles from the surface of the coarser carrier particles so that delivery to the lung can be facilitated.

A further aspect of the invention is a Raman spectroscopic system comprising a Raman analyzer, a non-contact probe, and a processing device. The Raman spectroscopic system is capable of directing electromagnetic radiation of the desired wavelength to the mixture and collecting the scattered radiation useful for analyzing the mixture of components both qualitatively and quantitatively.

The Raman spectroscopic system may include, for example, a Kaiser Raman RXN2™ analyzer (Kaiser Optical Systems, Inc.; Ann Arbor, Michigan) connected to a fiber optic probe and to a computer system. Laser light emitted from the analyzer is transmitted though fiber optic cables to and from the probe. In addition to the laser, the Raman analyzer contains a spectrograph and a charge-coupled device (CCD) detector. The spectrograph separates incoming light from the probe into distinct wavelengths. The diffracted light from the spectrograph is focused onto the surface of a 2-D array CCD detector, which measures the intensity of Raman scattered light. The output signal from the detector is amplified and processed to produce the Raman spectrum, which graphs optical intensity on the vertical axis and energy difference between the incident light and the scattered light on the horizontal axis. The computer system includes a computer, monitor, keyboard, mouse and software, which is used to control the Raman RXN2 base unit, provide basic data presentation and analysis, and communicate with other data analysis packages.

In a preferred embodiment, the probe is a non-contact probe positioned such that the sample falls within the focal point of the probe. The probe is connected to the Raman analyzer using a fiber optic cable that contains excitation (laser out) and collection (signal in) fibers. Typically, laser light is injected into one or more emission fibers which carries the laser excitation to a probe head and light is focused onto the sample. Light collected from the sample by the probe head is filtered to remove reflected laser light and Rayleigh scatter, and then travels down the collection fiber to the spectrograph in the analyzer. An example of a suitable probe for non-contact sampling is the PhAT probe (Kaiser Optical Systems, Inc.; Ann Arbor, Michigan).

For noninvasive monitoring of the powder mixture during blending, the vessel may be adapted to include ports or windows. The windows may be composed of light transmissible material such as borosilicate glass, quartz, or sapphire. For example, a sapphire window can be incorporated on the blending vessel at a fill line level to ensure that the window is covered.

In a typical Raman spectroscopy measurement, a sample is probed with intense monochromatic light (usually laser) resulting in elastic (Rayleigh scattering) and inelastic (Raman scattering) scattering of photons. Elastically scattered photons are at the same wavelength as the probing light and do not exchange energy with the sample molecules. These photons do not contribute to the Raman spectroscopy studies. However, inelastically scattered photons (i.e., Raman scatter) have lost energy (Stokes) or gained energy (Anti-Stokes) energy during this interaction) and carry information about the identity of the material as well as its chemical and physical structure. The Raman scattered signal is about $10^6$ to about $10^8$ times weaker than the Rayleigh scattered signal. Therefore, the broadband signal having the Raman and Rayleigh signal is broken down to its spectral components by a spectrograph, and the light intensity at each wavelength is analyzed by a photodetector.

Generally, the irradiating light comprises a wavelength in the range of about 400 nm to about 1200 nm. Preferably, the irradiating light comprises a wavelength in the range of about 650 nm to about 900 nm. More preferably, the irradiating light comprises a wavelength in the range of about 760 nm to about 800 nm. Even more preferably, the irradiating light comprises a wavelength of about 785 nm.

The non-contact probe can be positioned near the blender vessel and directed at, for example, an optical port composed of sapphire or other like material to enable remote monitoring. Generally, the non-contact probe is positioned about 1 mm to about 50 mm from the vessel. The non-contact probe may have a nominal beam diameter from about 3 mm to about 6 mm, and a nominal focal length from about 120 mm to about 250 mm.

During the blending process, Raman spectra may be collected at intervals of about 2 seconds to about 60 seconds. Preferably, the Raman spectroscopic data is acquired at intervals of about 14 seconds. The Raman spectra may be acquired with an exposure time of about 5 seconds to about 30 seconds. Preferably, the Raman spectroscopic data is acquired with an exposure time of about 10 seconds to about 30 seconds.

In an embodiment, the Raman spectroscopic data is acquired with about 1 scan to about 12 scans per minute. Preferably, a minimum of 2 to 6 scans per minute will be available to interpret blend mixing efficiency.

In an embodiment, the collected Raman spectroscopic data comprises wavenumbers of about 50 cm$^{-1}$ to about 5000 cm$^{-1}$. Preferably, the collected Raman spectroscopic data comprises wavenumbers of about 200 cm$^{-1}$ to about 3,500 cm$^{-1}$, about 400 cm$^{-1}$ to about 3,000 cm$^{-1}$, or about 500 cm$^{-1}$ to about 2,000 cm$^{-1}$. In a preferred embodiment, the Raman spectroscopic data comprises wavenumbers of about 175 cm$^{-1}$ to about 1875 cm$^{-1}$.

Raman spectroscopic data can be analyzed by a number of different chemometric techniques, including both univariate and multivariate methods. See, e.g., Smith, T., Innovations in Pharma Tech, 2012, 42: 28-33 "Chemometric Analysis of Raman Spectroscopy Data". The analysis can involve, for example, evaluating a peak number, peak intensity, peak position, peak shape, peak width, or any combination thereof within a defined wavenumber range of a Raman spectrum for the individual component in the dry powder.

An example of a univariate method to quantitatively discriminate complex Raman spectra is disclosed in Camerlingo, et al., Sensors, 2011, 11(9): 8309-8322, "Micro-Raman Spectroscopy and Univariate Analysis for Monitoring Disease Follow-Up". This method is based on the calculation of $R^2$ determination coefficient. One limitation of univariate methods is that it does not allow for comparing multiple time points simultaneously.

Preferably, the Raman spectroscopic data is analyzed using a multivariate method. Multivariate methods allow analysis of multiple spectra simultaneously and interdependently. This then allows for comparisons to be made between spectra and groups of spectra in a dataset and to identify trends. Suitable methods for multivariate analysis include, but are not limited to, a partial least squares regression analysis, a partial least squares discriminant analysis, an artificial neural network analysis, a classical least squares analysis, a principal component analysis (PCA), and a multiple linear regression. Multivariate analysis of Raman spectroscopy data is described in, for example, Haydock, R., "Multivariate analysis of Raman spectroscopy data," PhD. Thesis, University of Nottingham, (2015), available on-line at http://eprints.nottingham.ac.uk/30697/1/0-Full_Thesis_Corrected_5.pdf.

In a preferred embodiment, the multivariate analysis is a principal component analysis. Principal Components Analysis (PCA) is a method which aims to reduce the dimensionality of the data to describe the variation present in a dataset. PCA describes the major sources of variability in the spectra with a small number of orthogonal axes, or principal components. Each spectrum is plotted as a single point in the multidimensional space, resulting in a cluster of single-point spectra in n-dimensional space. The first principal component describes the largest source of spectral variation, the second axis describes the second greatest source, etc.

In one embodiment, variability in principal component scores can be used to determine blend homogeneity as a function of blender speed. In another embodiment, variability in principal component scores can be used to determine blend homogeneity as a function of concentration of the APIs.

Optionally, the Raman spectroscopic data can be preprocessed before it is analyzed. Spectral preprocessing can be used, for example, to enhance subtle differences between spectra by reducing the effects of unwanted signals from detector noise, fluorescence, laser power fluctuations, etc. Methods for preprocessing the Raman spectroscopic data include, but are not limited to, first-order derivatives, second-order derivatives, de-trending, Standard Normal Variate (SNV), Multiplicative Scatter Correction (MSC), Extended Multiplicative Signal Correction (EMSC), Orthogonal Signal Correction (OCS), Generalized Least Squares (GLS), spectral truncation, and combinations thereof. Preferably, the method for preprocessing the Raman spectroscopic data is a Multiplicative Signal Correction (MSC) on the spectroscopic data.

In another aspect of the invention, verification of the chemometric analysis for blend uniformity can be determined by off-line analysis using, for example, high performance liquid chromatography (HPLC).

The inventive method can be used with a wide variety of active pharmaceutical ingredients (APIs) suitable for use in a dry powder for inhalation. In one embodiment, the API can be a bronchodilator. The bronchodilator may be a Short-Acting Beta Adrenoceptor Agonist (SABA), such as albuterol, bitolterol, fenoterol, isoproterenol, levalbuterol, metaproterenol, pirbuterol or procaterol, a Long Acting Beta Adrenoceptor Agonist (LABA) such as arformoterol, bambuterol, clenbuterol, formoterol or salmeterol, or an Ultra Long Acting Beta Adrenoceptor Agonist (Ultra-LABA), such as abediterol, carmoterol, indacaterol, olodaterol or vilanterol. In another embodiment, the API may be an anticholinergic agent that blocks the activity of the muscarinic acetylcholine receptor, including a Short-Acting Muscarinic Antagonist (SAMA) such as ipratropium, or a Long-Acting Muscarinic Agent (LAMA), such as aclidinium, glycopyrronium, tiotropium, and umeclidinium. In another embodiment, the API may be an inhaled corticosteroid (ICS) such as, for example, budesonide, ciclesonide, flunisolide, beclomethasone, fluticasone, mometasone or triamcinolone. In other embodiments, the API is a pharmaceutically acceptable salt of any of the above-mentioned APIs. In another embodiment, the API is another powder API known in the art or later discovered, or mixtures of one or more of any of the above-mentioned APIs.

As discussed herein, conventional DPI formulations utilize active pharmaceutical ingredients that are micronized. Prior to blending with the excipient (carrier agent), the API may include micronized particles wherein at least 90% of the particles, preferably at least 92% of the particles, and more preferably at least 95% of the particles, have a particle size (D90) less than about 10 microns, preferably less than about 8 microns, and more preferably, less than about 6 microns.

In one embodiment, prior to blending with the excipient (carrier agent), the API includes micronized particles having an aerodynamic diameter between about 0.05 microns to about 20 microns, preferably between about 0.1 microns to about 15 microns, and more preferably between about 0.2 microns to about 10 microns.

In one embodiment, the particle size (D90) of the carrier agent is less than 1000 microns. Preferably, the particle size (D90) of the excipient (carrier agent) is in the range from about 50 to about 400 microns, and more preferably from about 100 to about 300 microns. In a preferred embodiment, the particle size (D90) of the carrier particles is about 150 microns. The relatively large diameter of the carrier particle improves the opportunity for drug particles to become attached to carrier particles to provide good flow and entrainment characteristics.

Typically, the amount of each individual API in the dry powder for inhalation is at least 0.01 wt. %. Each of the at least 2 APIs in the dry powder for inhalation can be present in an amount from about 0.05 wt. % to about 5 wt. %, from about 0.05 wt. % to about 2.5 wt. %, or from about 0.1 wt. % to about 2.5 wt. %. Preferably, each of the at least 2 APIs in the dry powder for inhalation can be present in an amount from about 0.1 wt. % to about 1 wt. %.

The excipient (carrier agent) can be any physiologically acceptable inert material of animal or vegetable origin. The carrier agent is typically a sugar, sugar alcohol, or an amino sugar. Sugars, sugar alcohols, and amino sugars are well known in the art and the embodiments are not restricted to any particular sugar, sugar alcohol or amino sugar. Preferably, the sugar is a monosaccharide such as arabinose, fructose, or glucose, or a disaccharide such as lactose, maltose, saccharose, sucrose, or trehalose. The carrier agent can also be one or more polyalcohols, such as lactitol, maltitol, mannitol, sorbitol, or xylitol, or an amino sugar, such as glucosamine. In one embodiment, the carrier agent is alpha-lactose monohydrate. Examples of commercially available alpha-lactose monohydrates include SpheroLac®, Pharmatose® and Lactohale®.

The carrier agent can be a mixture of fine carrier particles and coarse carrier particles, preferably of the same kind. When a mixture of fine carrier particles and coarse carrier particles is used, the fraction of fine carrier particles in coarse carrier particles is in the range of 0.1 wt. % to 20 wt. %, preferably in the range of 0.5 wt. % to 18 wt. %, and more preferably in the range of 1.0 wt. % to 15 wt. %.

When the dry powder for inhalation comprises APIs that have high physiological activity, more of the carrier agent will be employed. The amount of carrier agent can be present in an amount from about 80 wt. % of the powder formulation. The carrier agent can be present in an amount from about 80 to about 99.9 wt. %, preferably from about 90 to about 99.9 wt. %, and more preferably from about 95 to about 99.9 wt. %.

The particles of the active agent and the carrier agent can be provided within the particle size ranges provided herein prior to blending. A number of techniques known to those skilled in the art for the production of solid materials of the required size can be used in certain aspects of the disclosure, including mechanical micronisation, milling, jet milling, grinding, rapid precipitation, freeze drying, lyophilization, rapid expansion of supercritical fluids, spray drying, and mixtures thereof.

Upon aerosolization, the particle size is expressed as mass aerodynamic diameter (MAD). The MAD indicates the capability of the particles of being transported in an air stream. The mass median aerodynamic diameter (MMAD) corresponds to the mass aerodynamic diameter of 50 percent by weight of the particles.

The powder formulations can be utilized with any type of DPIs known in the art. DPIs can be divided into two basic types: (i) single dose inhalers, for the administration of pre-subdivided single doses of the active compound; and (ii) multidose dry powder inhalers (MDPIs), either with pre-subdivided single doses or pre-loaded with quantities of active ingredient sufficient for multiple doses. DPIs can be further classified on the basis of the required inspiratory flow rates (L/min), which in turn depend on their design and mechanical features. Thus, DPIs can be classified as: (i) low-resistance devices (>90 L/min); (ii) medium-resistance devices (about 60 L/min); and (iii) high-resistance devices (about 30 L/min). The powder formulations of the invention preferably are administered with a medium-resistance or a high-resistance multidose device.

Another consideration with respect to the development and manufacture of a dry powder for inhalation is the use of continuous manufacturing. Although pharmaceutical products have historically been manufactured by a "batch" process, there is nothing in FDA regulations that prohibits their manufacture by a "continuous" process. Indeed, continuous manufacturing (CM) has the potential to lower capital costs, reduce inventory, and increase process efficiency among other benefits.

The vast majority of powder blending processes in the pharmaceutical industry are batch based. Here, the required quantities of each ingredient are added to a process vessel, which delivers a fixed mass of blended material at the conclusion of its operating cycle. There have been recent efforts to develop continuous blending processes, which rely on the behavior of powder feeder systems and the blending apparatus itself to act in a controllable manner, delivering blended material at a mass per unit time basis.

In one embodiment, the method is used in a development process or a commercial process. In another embodiment of the invention, the method is used in a batch process, a semi-continuous process, or a continuous process.

The methods disclosed herein may be implemented in a number of ways. Certain embodiments may be implemented using hardware, software, or a combination thereof. When implemented with software, the software code can be executed on any suitable processor or collection of processors. The processors may be provided in a single computer or distributed among multiple computers. Such processors may be implemented as integrated circuits.

A computer may be embodied in a number of forms. Suitable computers include, but are not limited to, a desktop computer, a laptop computer, a rack-mounted computer, or a tablet computer. A computer may be embedded in a device with suitable processing capabilities, including a tablet, smart phone, or any other suitable electronic device.

A computer may have one or more input or output devices which can be used, for example, to present a user interface. Examples of input devices suitable for use as a user interface include keyboards, mice, touch pads, and tablets. Examples of output devices suitable for use as a user interface include printers, monitors, display screens, speakers, and the like.

The methods described herein may be coded as software that is commercially available or written using any number of suitable programming languages, such as MATLAB (MathWorks; Natick, Mass.). One example of commercially available software which provides a means for rapid instrument configuration, data acquisition, and univariate data analysis is iC Raman™ 4.1 software (Kaiser Optical Systems, Inc.; Ann Arbor, Michigan). For spectral preprocessing, various software can be employed. For complex chemometric analysis using multivariate methods, suitable commercial software includes, but is not limited to SIPAT™ (Siemens), BioPAT® (Sartorius), and GRAMS IQ™ (Thermo Fisher Scientific).

Having described the invention in detail, it will be apparent that modifications and variations are possible without departing from the scope of the invention defined in the appended claims.

EXAMPLES

The following non-limiting examples are provided to further illustrate the present invention.

Materials

Micronized fluticasone propionate (D90=2.5 microns to 6 microns), micronized salmeterol xinafoate (D90=2.5 microns to 6 microns), micronized albuterol sulfate (D90=2.5 microns to 6 microns), and alpha-lactose monohydrate (D90=100 microns to 300 microns) were used. The formulations used in these experiments are representative of dry powder inhaler formulations used in commercial pharmaceutical manufacturing.

Figure 1B:
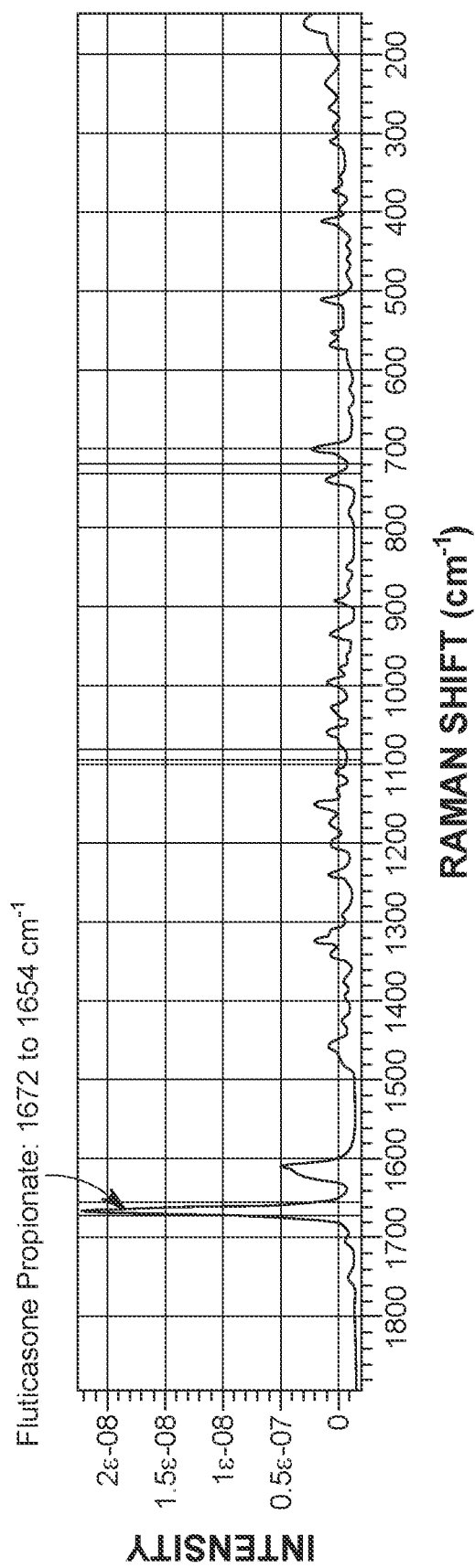
Figure 1C:
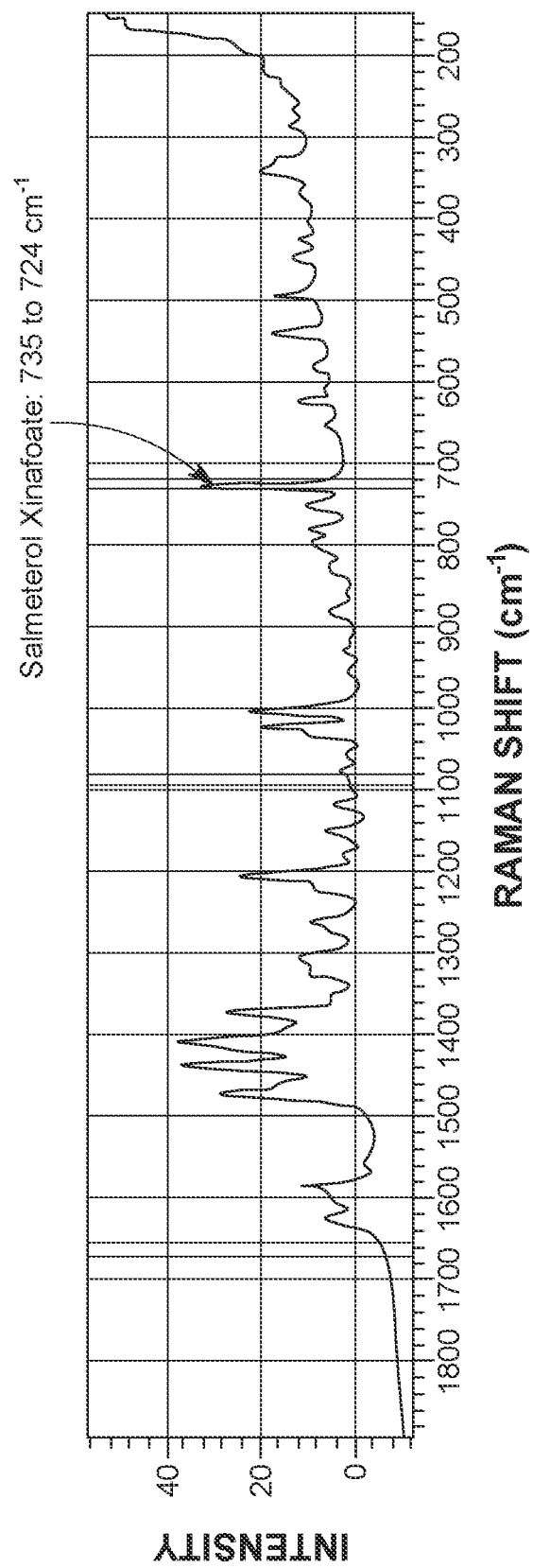
Figure 2A:
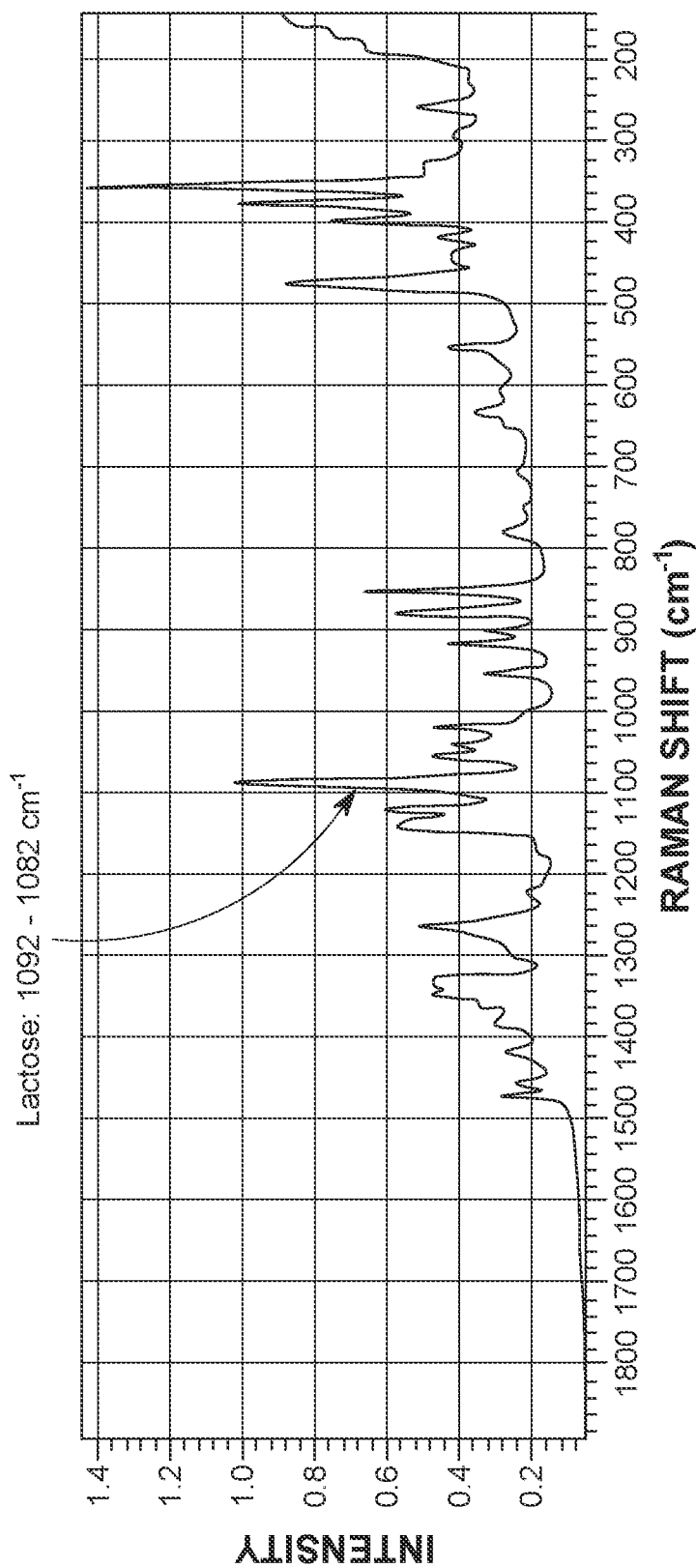
FIGS. 2A-2C show the individual Raman spectrum for each component in the Fluticasone Propionate-Albuterol Sulfate blend, with assignment of characteristic peaks, in accordance with one or more embodiments.
Figure 2B:
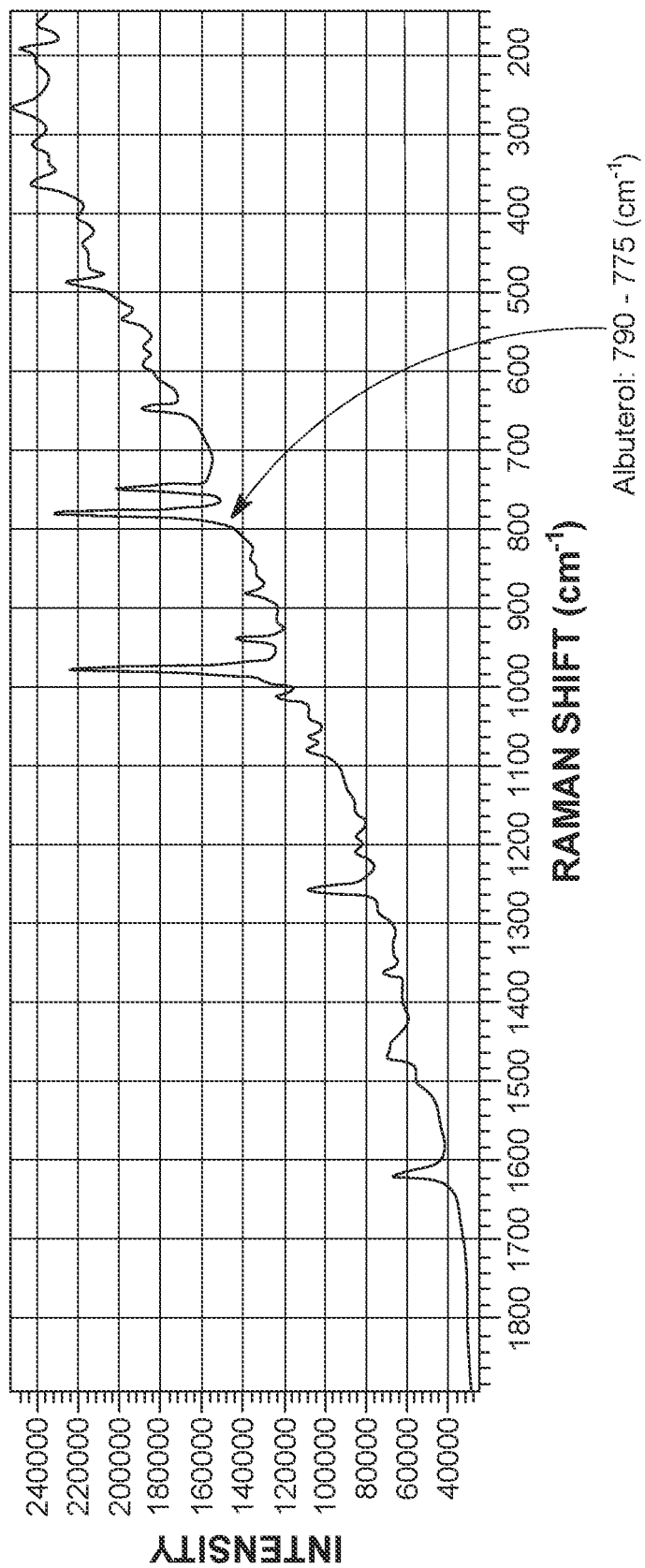
Figure 2C:
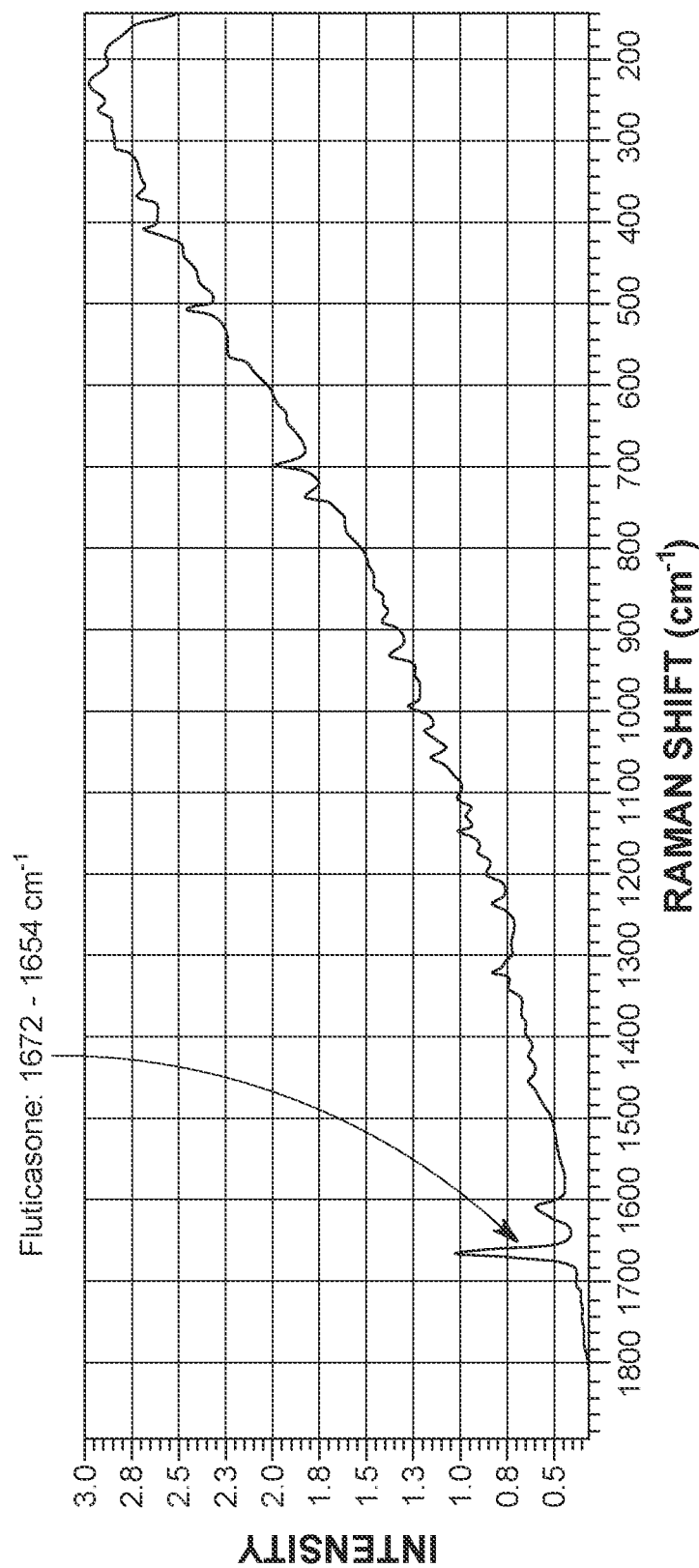

A Raman spectrum for each component was collected prior to the blending experiments. The Raman spectra for the components were compared to one another to identify Raman peaks exclusive to each component. As shown in FIG. 1, the Raman spectrum of α-lactose monohydrate did not interfere with the characteristic Raman peaks of fluticasone propionate (1672-1654 $cm^{-1}$) or salmeterol xinafoate (735-724 $cm^{-1}$). As shown in FIG. 2, the Raman spectrum of α-lactose monohydrate did not interfere with the characteristic Raman peaks of fluticasone propionate (1672-1654 $cm^{-1}$) or albuterol sulfate (790-775 $cm^{-1}$).

Equipment

The Raman spectroscopic system used in these experiments was a Kaiser Raman RXN2™ Hybrid analyzer equipped with a 785 nm Invictus Class B Laser, a PhAT non-contact probe for solids analysis (6 mm spot size; spectral coverage 175 $cm^{-1}$ to 1875 $cm^{-1}$).

Software

The Raman spectra were collected using HoloGRAMS software installed on the Raman RXN2 analyzer. Data review and analysis was performed using iC Raman™ 4.1 software (Kaiser Optical Systems, Inc.; Ann Arbor, MI). Standard normal variant pre-processing and multivariate calibration and analysis of Raman spectra were performed using area under the curve and chemometric analysis, respectively.

Experiment 1: In-line Raman Spectroscopy Used to Monitor Blending of Fluticasone Propionate, Salmeterol Xinafoate, and Lactose Monohydrate In a first experiment, the active ingredients fluticasone propionate and salmeterol xinafoate were used to manufacture two dry powder blends. α-Lactose monohydrate was the only excipient (carrier agent) in the blend. The impact of blender speed was assessed in Part A and Part B of the experiment, as shown in Table 1 below.

TABLE 1

Variables for Experiment 1

| Experiment | Component | Wt. % | Blender Speed (rpm) | Collection Time (min) |
|---|---|---|---|---|
| 1A (low speed) | fluticasone propionate | 0.82 | 450 | 30 |
| | salmeterol xinafoate | 0.58 | | |
| | α-lactose monohydrate | 98.6 | | |
| 1B (high speed) | fluticasone propionate | 0.82 | 1250 | 30 |
| | salmeterol xinafoate | 0.58 | | |
| | α-lactose monohydrate | 98.6 | | |

A 2 L stainless steel blender bowl having a sapphire window incorporated on the side to enable remote monitoring was charged with fluticasone propionate, salmeterol xinafoate and α-lactose monohydrate (see amounts in Table 1). The components were blended using a high shear mixer. In Experiment 1A, the components were blended at low speed (450 rpm) for a total of 30 minutes. In Experiment 1B, the components were blended at high speed (1250 rpm) for a total of 30 minutes.

During the blending process, Raman spectra were collected with an exposure time of 14 seconds and a phase interval of 30 seconds. Peak area as a function of time was calculated using iC Raman™ 4.1 software. The relative standard deviation (RSD) was calculated for the peak areas at time intervals. Chemometric analysis of spectra was also carried out. Principle component (PC1) scores were calculated to compare the spectra collected through the blending process.

Figure 3A:
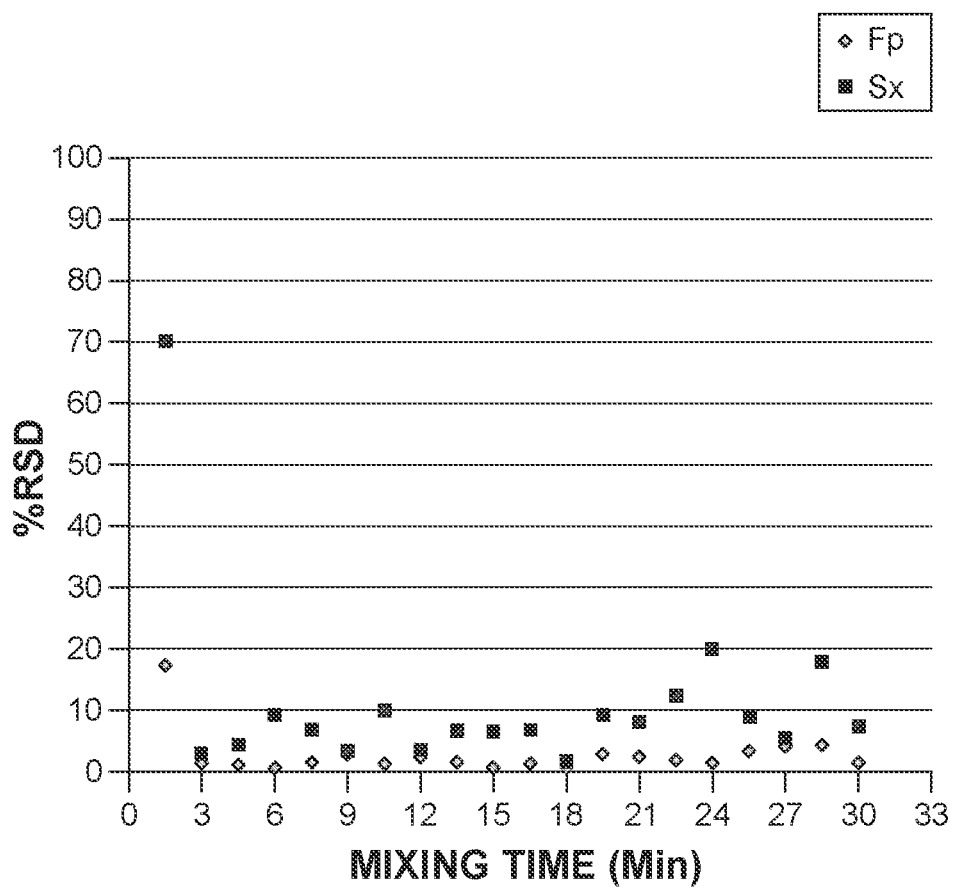
FIG. 3A shows a graph depicting the Percent Relative Standard Deviation (% RSD) of the peak area of Fluticasone Propionate and Salmeterol Xinafoate during the high speed blending process, in accordance with one or more embodiments.
Figure 3B:
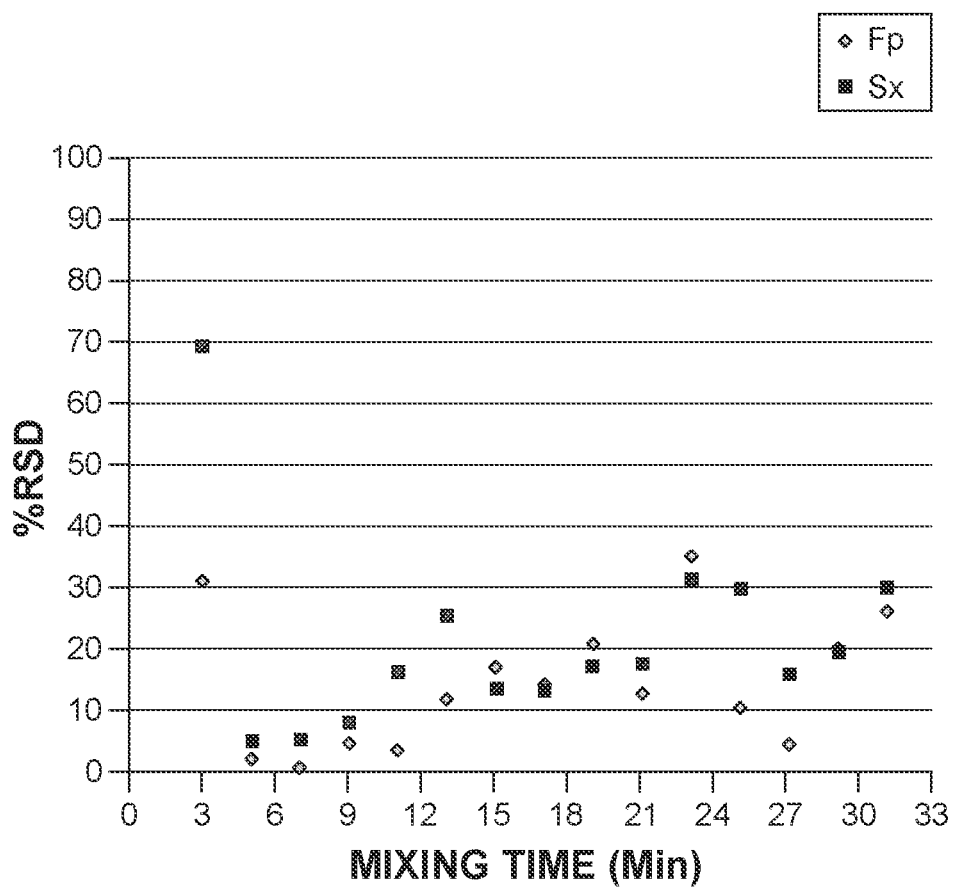
FIG. 3B shows a graph depicting the Percent Relative Standard Deviation (% RSD) of the peak area of Fluticasone Propionate and Salmeterol Xinafoate during the low speed blending process, in accordance with one or more embodiments.

The results of the first experiment suggested that the RSD of the peak areas of fluticasone propionate was consistently below 5% between the mixing time of 3 minutes and 30 minutes (FIG. 3). It took about 3 minutes of mixing time for fluticasone propionate to reach a homogeneous state. On the other hand, the RSD of the peak areas of salmeterol xinafoate varied at different time intervals. The RSD of salmeterol xinafoate was below 10% between the mixing time of 3 minutes and 20 minutes. This indicated that mixing was less variable between 3 and 20 minutes.

Figure 4:
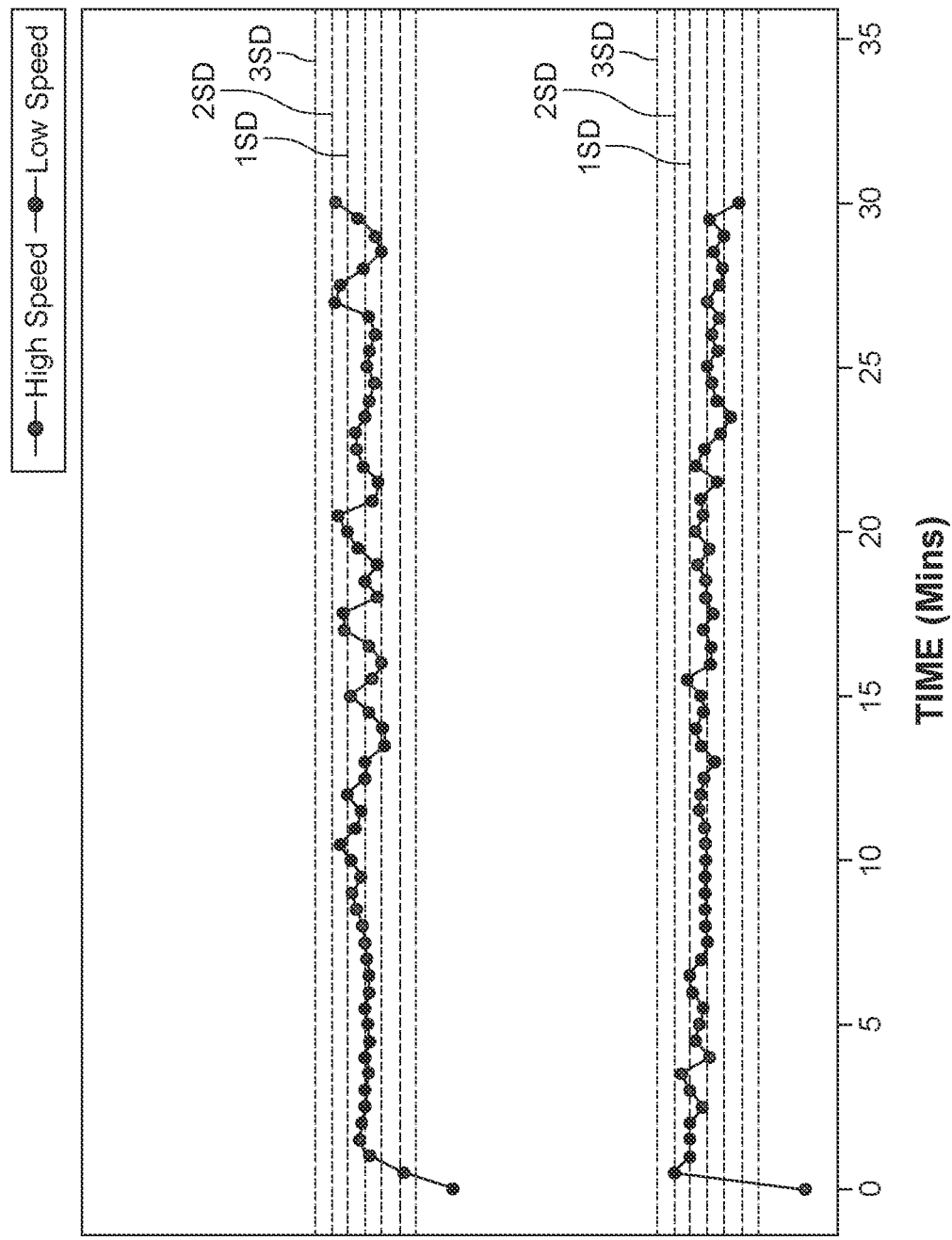
FIG. 4 shows a graph depicting the Principal Component (PC1) score comparison of Fluticasone Propionate at two different blender speeds, in accordance with one or more embodiments.
Figure 5:
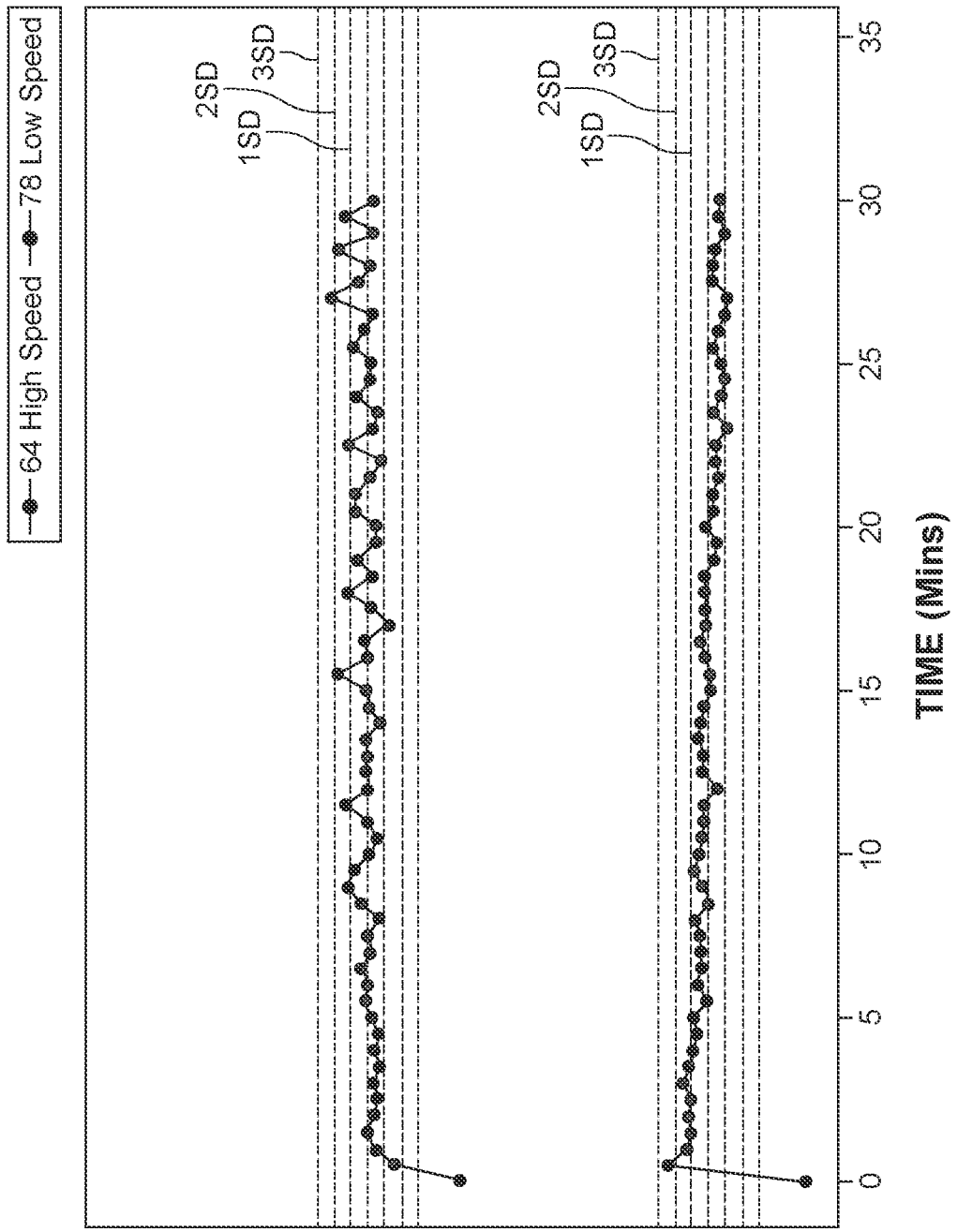
FIG. 5 shows a graph depicting the Principal Component (PC1) score comparison of Salmeterol Xinafoate at two different blender speeds, in accordance with one or more embodiments.

Chemometric analysis was carried out to compare the PC1 scores at two different speeds. It was found that lower speed blending had more variable PC1 scores within 2 standard deviations compared to higher speed blending for fluticasone propionate (FIG. 4). Similar results were also observed for salmeterol xinafoate (FIG. 5). This suggested that blend was more homogeneous when mixed at a higher speed.

Blend uniformity was determined according to the FDA, "Guidance for Industry; Powder Blends and Finished Dosage Units— Stratified In-Process Dosage Unit Sampling and Assessment," October 2003, available at https://www.fda.gov/ohrms/dockets/98fr/03d-0493-gd10001.pdf. Accordingly to the FDA guidelines, blend uniformity is assessed by collecting and assaying 10 samples from 10 sampling locations in the blender. The mean and relative standard deviations (RSD) of all individual results are calculated. To meet Tier 1 criteria, the RSD of all individual results is ≤5.0% and all individual results are within 10.0% (absolute) of the mean of the results. In the event of not meeting Tier 1 acceptance criteria, an additional 2 samples from each of the 10 locations are sampled and assayed according to Tier 2 criteria.

Figure 6:
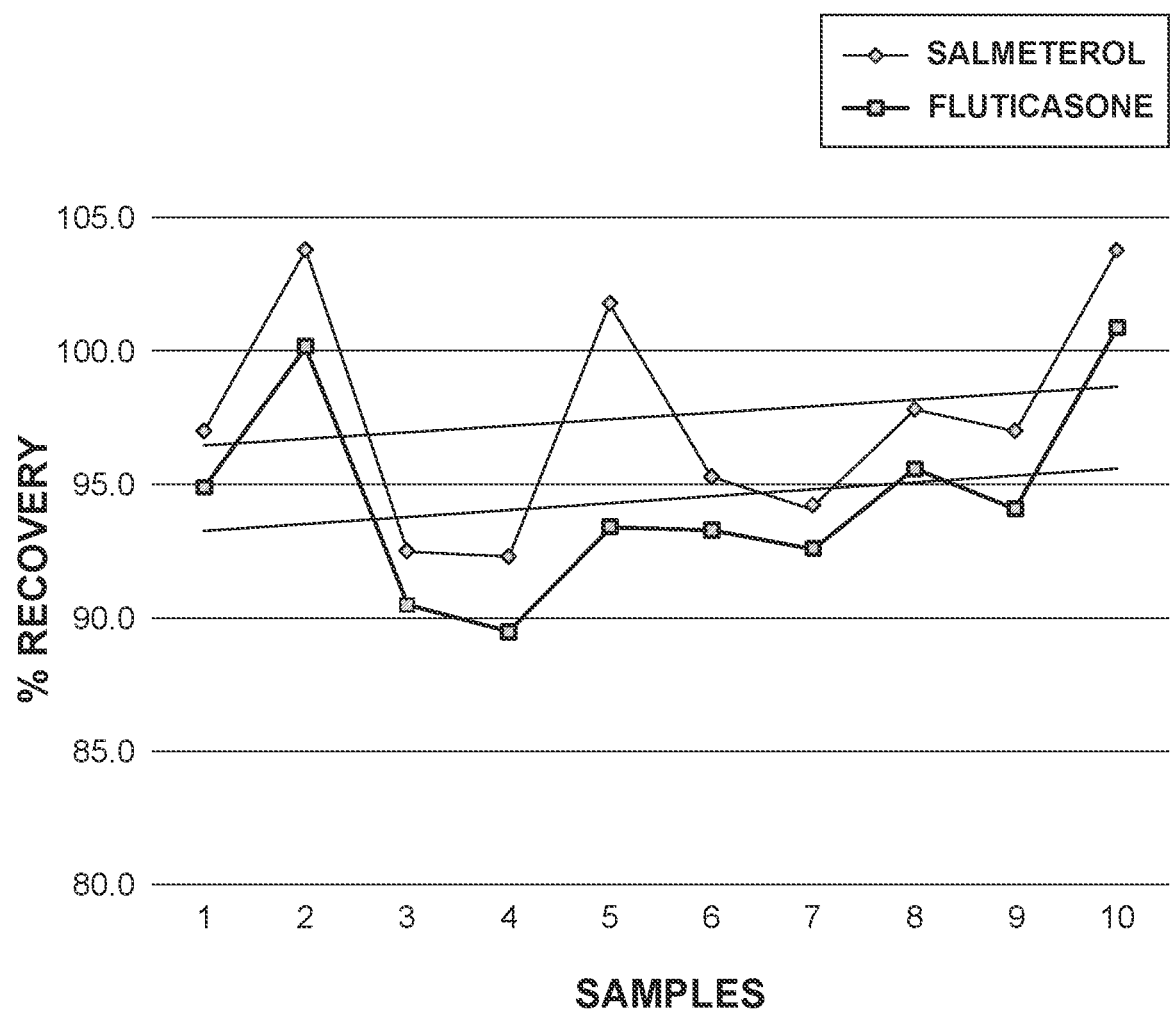
FIG. 6 shows a graph depicting the percent recovery of Fluticasone Propionate and Salmeterol Xinafoate from 10 different locations of blend manufactured at high speed, in accordance with one or more embodiments.

After completion of Experiment 1B, samples were collected from the stationary powder blend in 10 different locations and analyzed by HPLC. The % recovery of fluticasone propionate and salmeterol xinafoate met FDA guidelines for blend uniformity (FIG. 6). This further validated the chemometric analysis that the blend was homogenous.

Experiment 2: In-line Raman Spectroscopy Used to Monitor Blending of Fluticasone Propionate, Albuterol Sulfate, and Lactose Monohydrate In a second experiment, the active ingredients fluticasone propionate and albuterol sulfate were used to manufacture three dry powder blends. α-Lactose monohydrate was the only excipient (carrier agent) in the blends. The effect of API concentration was assessed in Parts A-C of the experiment. Three different blends containing three different concentrations of fluticasone propionate and albuterol sulfate were blended at high speed, as shown in Table 2 below.

TABLE 2

Variables for Experiment 2

| Experiment | Component | Wt. % | Blender Speed (rpm) | Collection Time (min) |
|---|---|---|---|---|
| 2A | fluticasone propionate | 0.25 | 1250 | 60 |
| | albuterol sulfate | 1.13 | | |
| | α-lactose monohydrate | 98.62 | | |
| 2B | fluticasone propionate | 0.375 | 1250 | 60 |
| | albuterol sulfate | 1.695 | | |
| | α-lactose monohydrate | 97.93 | | |
| 2C | fluticasone propionate | 0.50 | 1250 | 60 |
| | albuterol sulfate | 2.26 | | |
| | lactose monohydrate | 97.24 | | |

A 2 L stainless steel blender bowl having a sapphire window incorporated on the side to enable remote monitoring was charged with fluticasone propionate, albuterol sulfate, and α-lactose monohydrate (see amounts in Table 2).

The components were blended using a high shear mixer at 1250 rpm for a total of 60 minutes. In Experiment 2A, the concentration of active ingredients was 0.25 wt. % fluticasone propionate and 1.13 wt. % albuterol sulfate. In Experiment 2B, the concentration of active ingredients was 0.375 wt. % fluticasone propionate and 1.695 wt. % albuterol sulfate. In Experiment 2C, the concentration of active ingredients was 0.50 wt. % fluticasone propionate and 2.26 wt. % albuterol sulfate.

During the blending process, Raman spectra were collected with an exposure time of 14 seconds and a phase interval of 30 seconds. Peak area as a function of time was calculated using iC Raman™ 4.1 software. The relative standard deviation (RSD) was calculated for the peak areas at intervals. Chemometric analysis of spectra was also carried out. Principle component (PC1) scores were calculated to compare the spectra collected through the blending process.

Figure 7A:
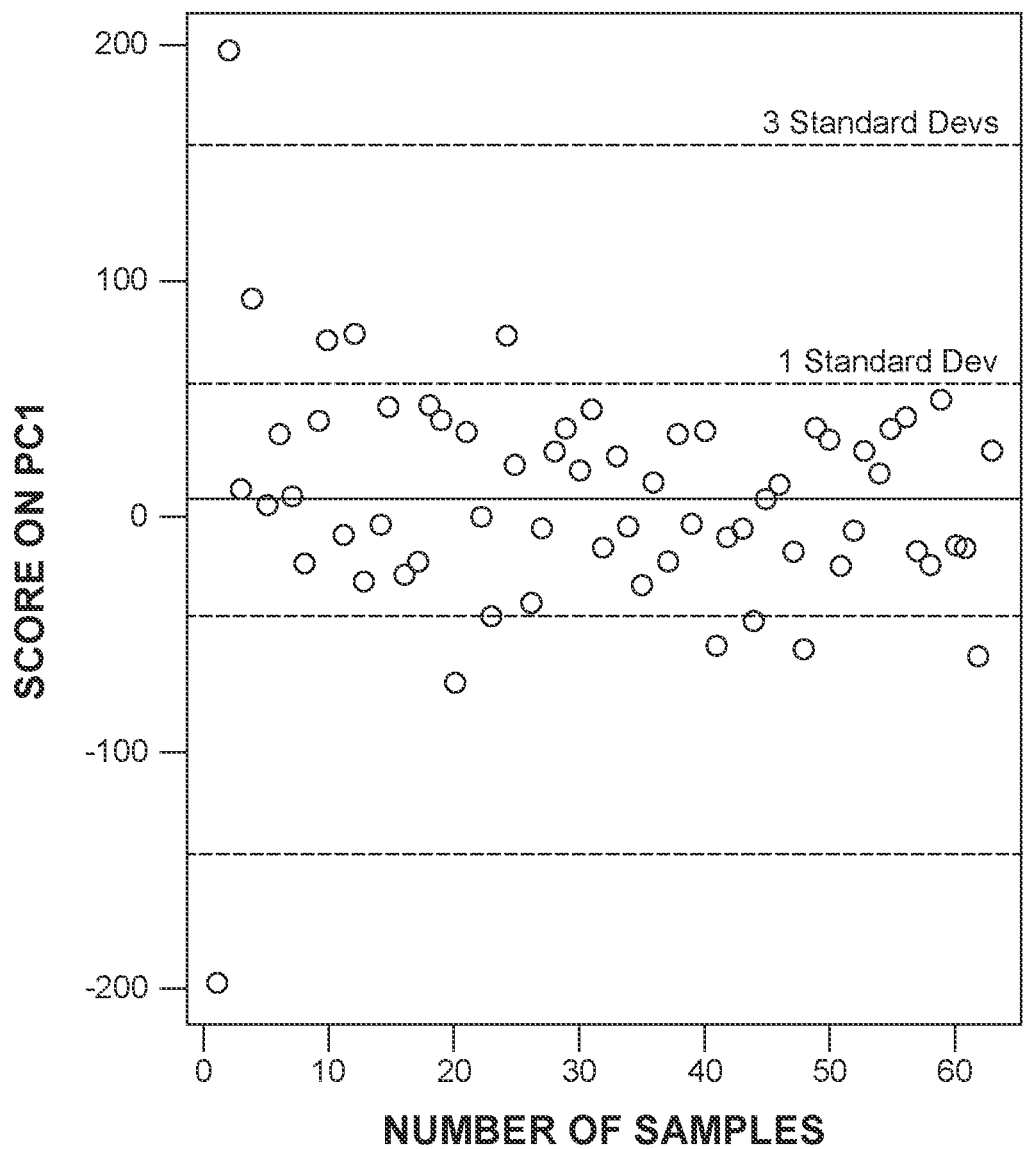
FIG. 7A shows a graph depicting the Principal Component (PC1) score comparison of Fluticasone Propionate at concentration A (0.25 wt. %), in accordance with one or more embodiments.
Figure 7B:
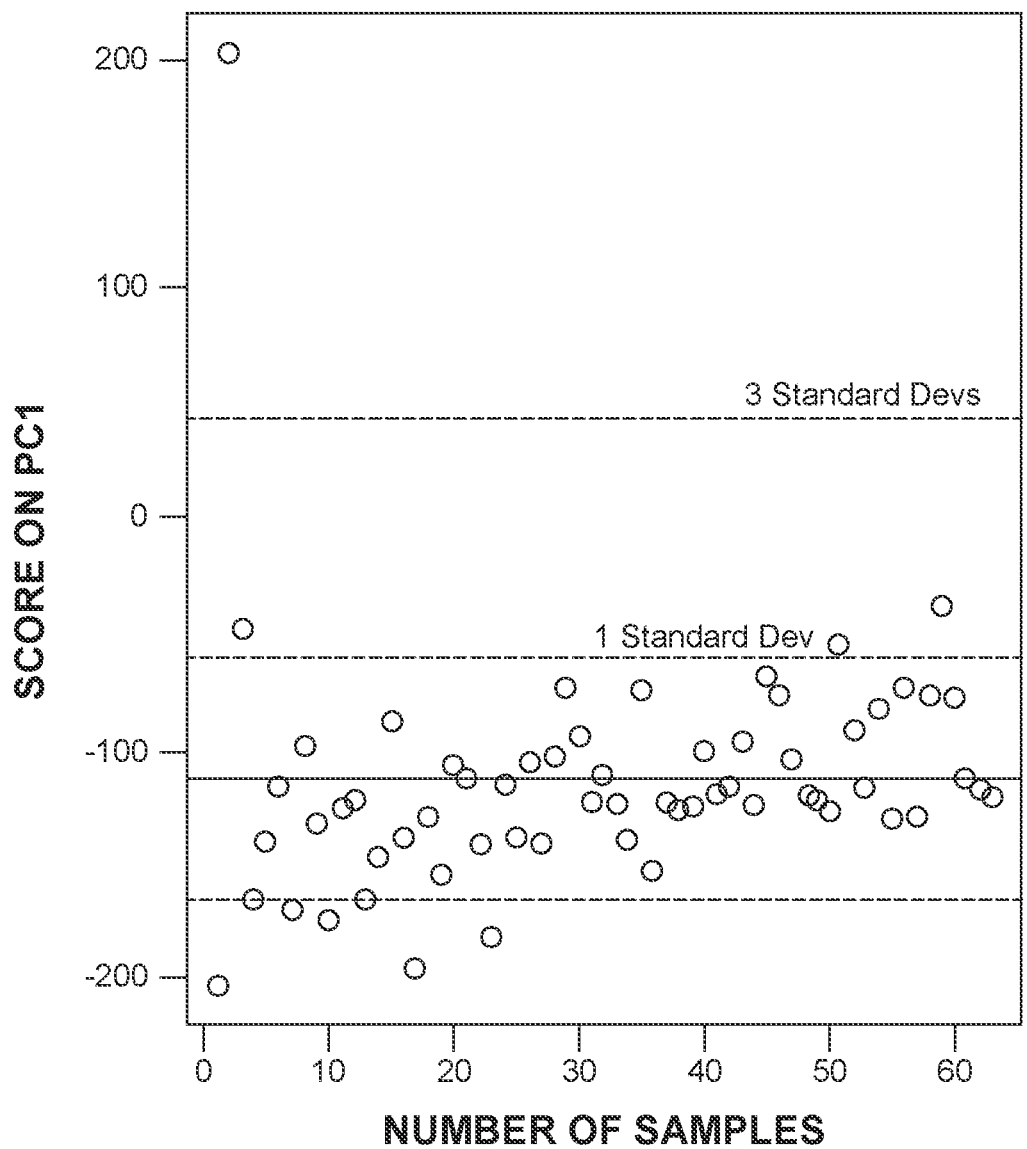
FIG. 7B shows a graph depicting the Principal Component (PC1) score comparison of Fluticasone Propionate at concentration B (0.375 wt. %), in accordance with one or more embodiments.
Figure 7C:
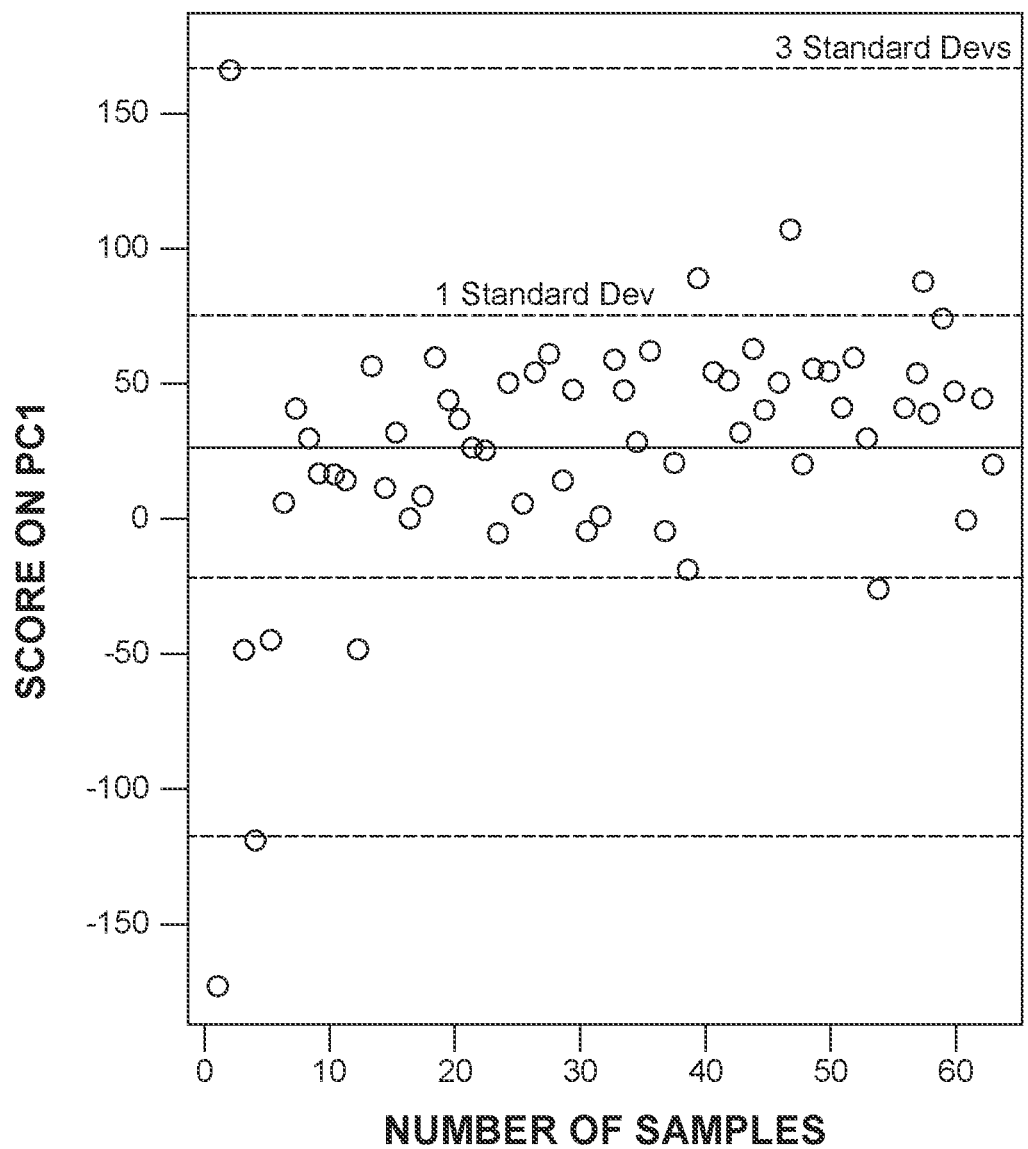
FIG. 7C shows a graph depicting the Principal Component (PC1) score comparison of Fluticasone Propionate at concentration C (0.50 wt. %), in accordance with one or more embodiments.
Figure 8A:
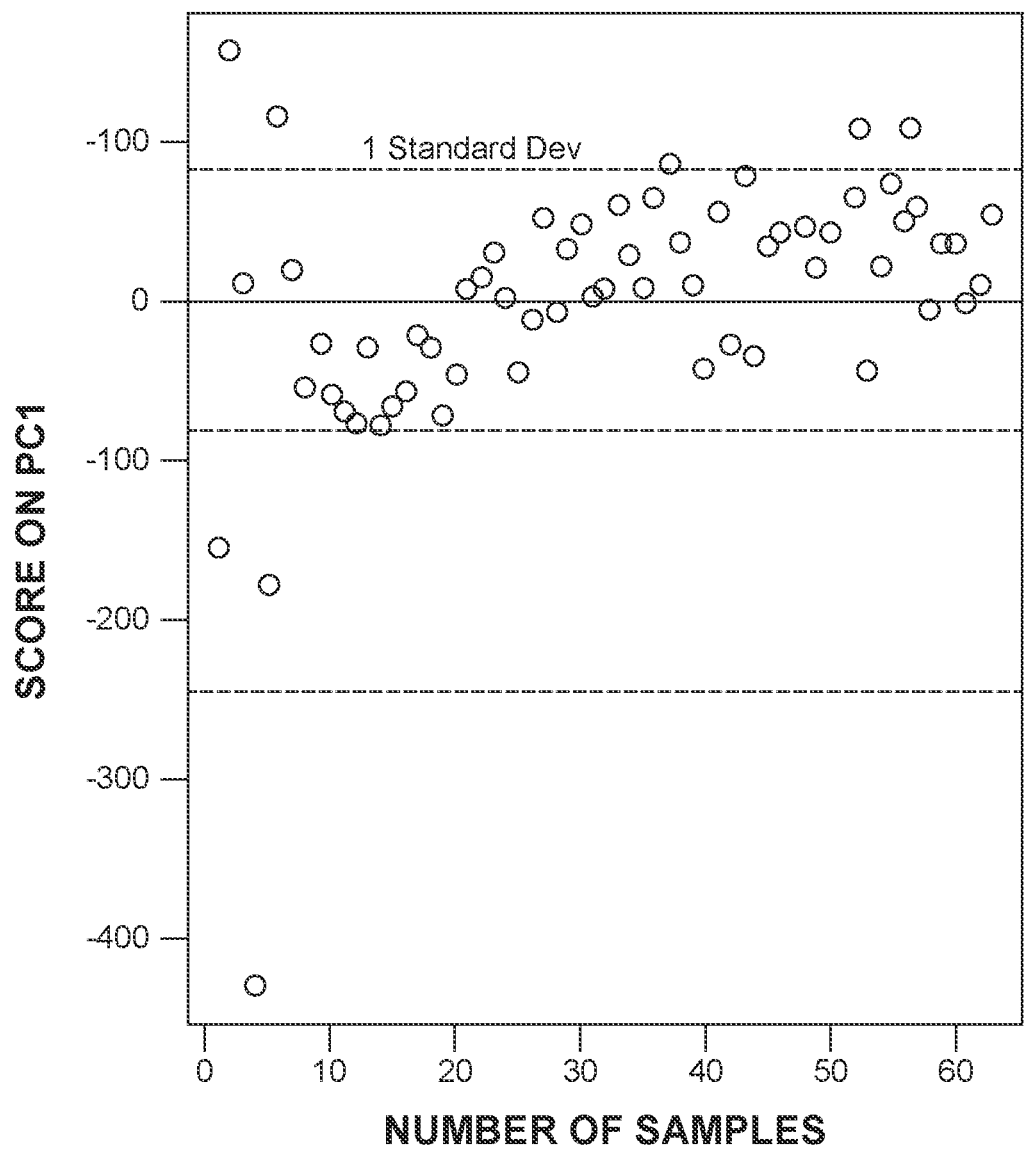
FIG. 8A shows a graph depicting the Principal Component (PC1) score comparison of Albuterol Sulfate at concentration A (1.13 wt. %), in accordance with one or more embodiments.
Figure 8B:
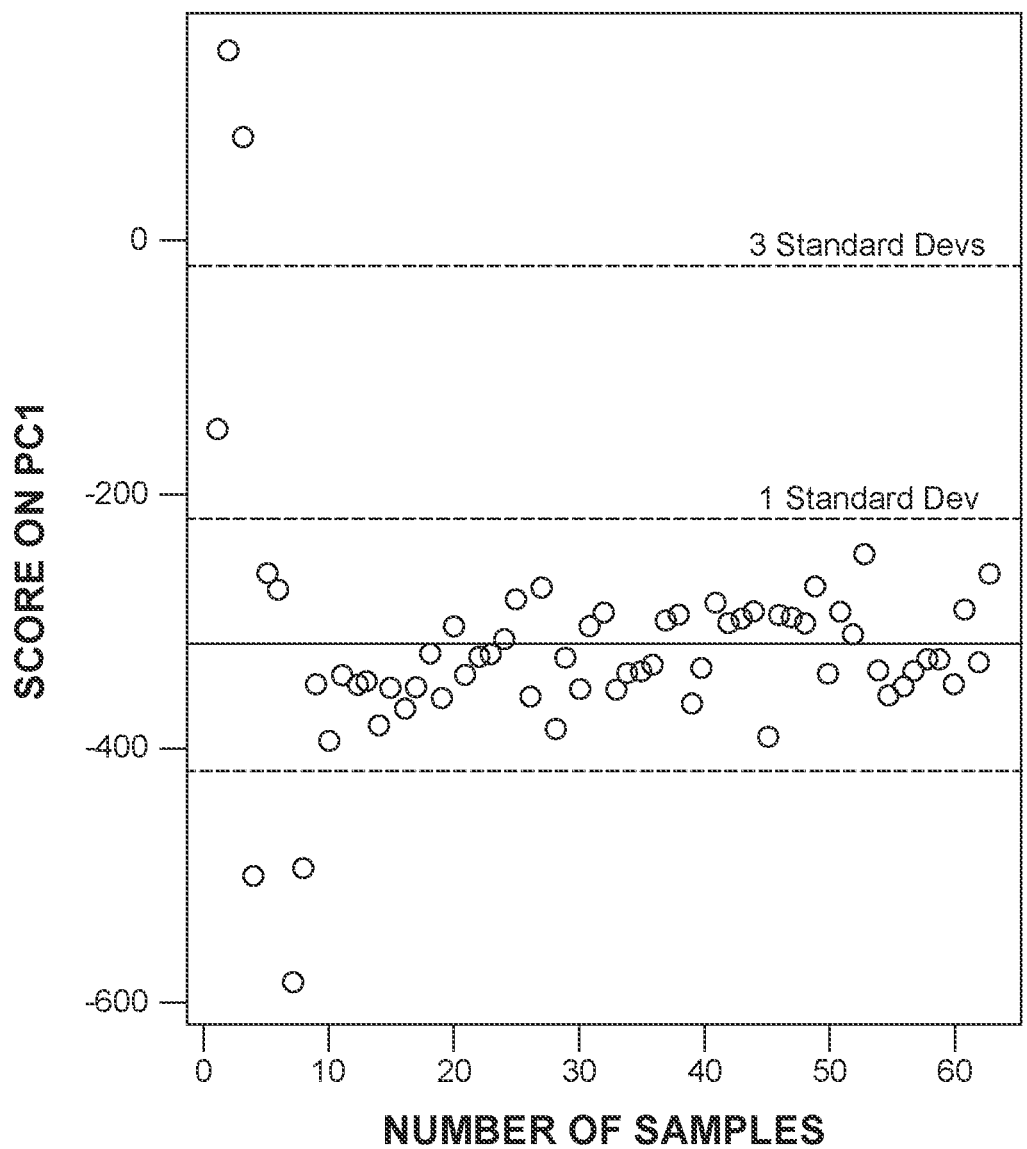
FIG. 8B shows a graph depicting the Principal Component (PC1) score comparison of Albuterol Sulfate at concentration B (1.695 wt. %), in accordance with one or more embodiments.
Figure 8C:
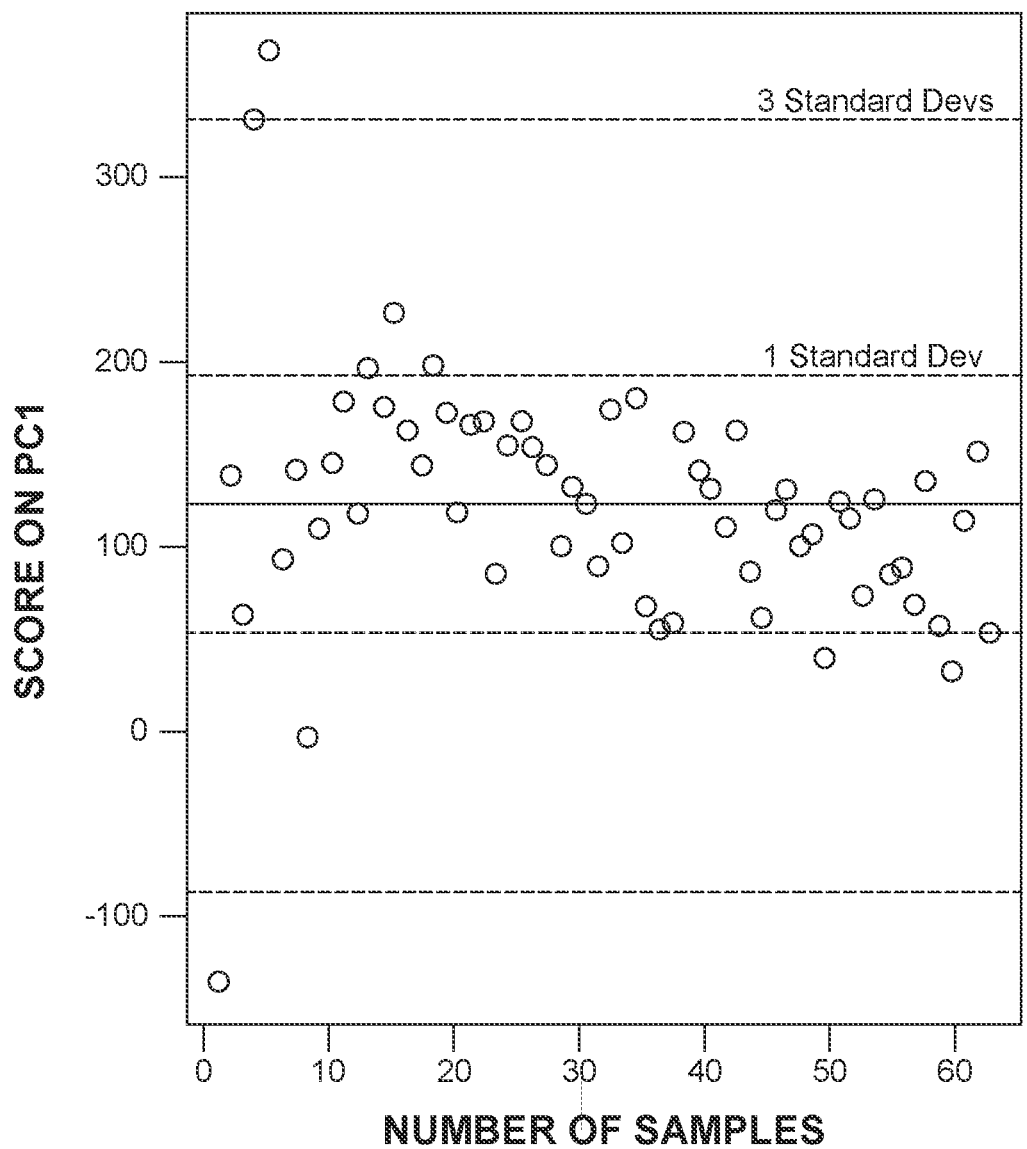
FIG. 8C shows a graph depicting the Principal Component (PC1) score comparison of Albuterol Sulfate at concentration C (2.26 wt. %), in accordance with one or more embodiments.
Figure 9:
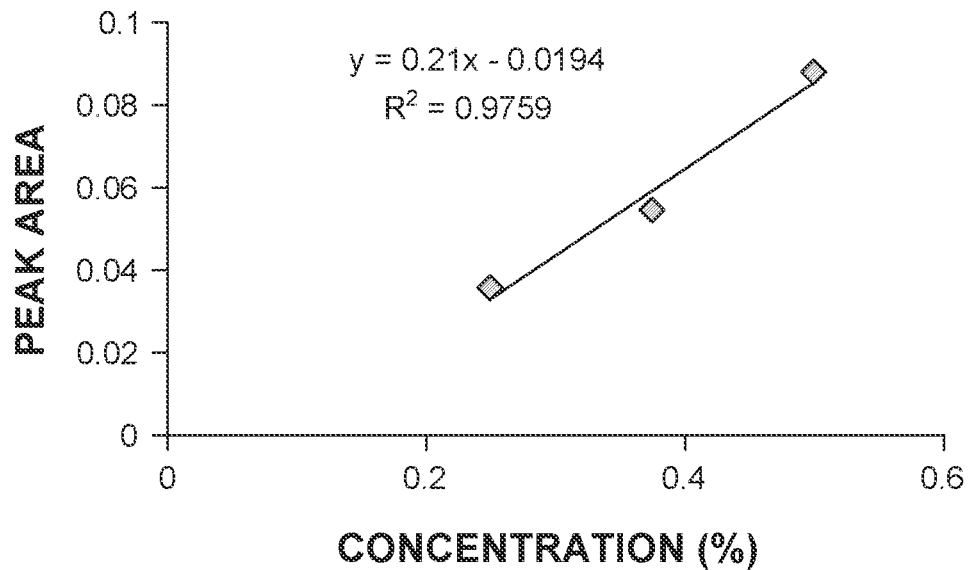
FIG. 9 shows a graph depicting the correlation of concentration and peak area of Fluticasone Propionate, in accordance with one or more embodiments.
Figure 10:
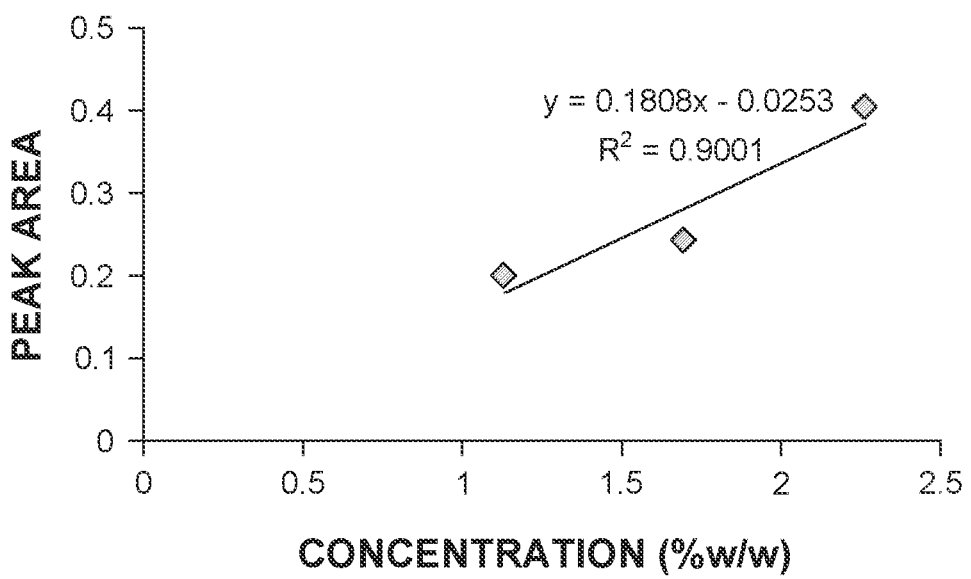
FIG. 10 shows a graph depicting the correlation of concentration and peak area of Albuterol Sulfate, in accordance with one or more embodiments.

The results of this experiment suggested that PC1 scores of fluticasone propionate at three different concentrations were within 1 standard deviation (FIGS. 7A-7C). Similar results were observed for albuterol sulfate at three different concentration level (FIGS. 8A-8C). This suggested that homogenous blends were obtained at all three concentrations levels. The peak area and concentration were correlated for fluticasone propionate (FIG. 9) and for albuterol sulfate (FIG. 10). A linear relationship was found for both molecules ($R^2 > 0.9$).

Accordingly, a dry powder inhalation product containing two different micronized active ingredients and lactose carrier particles was manufactured using in-line Raman spectroscopy to monitor the blending step. A Raman RXN2 analyzer equipped with a PhAT probe head for noncontact sampling was utilized to collect the spectra of the blends over a specific duration. Characteristic peaks in the Raman spectra of the two active ingredients were identified and distinguished from each other and the excipient, which allowed for spectral differences of the active ingredients to be monitored during blending. The peak area for the active ingredients was determined during the blending process using iC Raman™ 4.1 software. The relative standard deviation (RSD) was calculated for the consecutive time points in order to determine the blend homogeneity of the two drug substances.

Application of Raman spectroscopy for in-line monitoring of powder blends involves a number of different variables, including exposure time, number of scans (or accumulations), and phase interval. The method will be specific for different applications and drug concentrations. A number of different iterations of these parameters were studied to analyze the active ingredients in the different blends. The optimized method utilized an exposure time of 14 seconds, 2 scans, and phase interval of 30 seconds. The concentration of both active ingredients in the blends manufactured was very low (<1 wt. %).

In the first experiment, it was found that the spectral region for fluticasone propionate and salmeterol xinafoate are unique, without any interference from the excipient α-lactose monohydrate. This was an important factor to differentiate the active ingredients and to detect both molecules while in-line monitoring of the blending process with the Raman spectroscopic system. Chemometrics analysis was also carried out to understand the blend homogeneity. It was found that a blend manufactured at a high speed was more homogenous compared to a blend manufactured at a low speed. The blend uniformity test was also carried out for a blend manufactured at high speed, which met the specification in the FDA Guidance. This result further validated that chemometrics is a useful tool to determine variability in principle component scores and to confirm blend homogeneity.

A significant aspect of the first experiment was our finding that extended blending times do not necessarily result in a homogenous blend. Competing with the powder mixing is segregation (demixing). For dry powder inhalation formulations, adherence of micronized drug particles onto larger carrier particles occurs during blending, but too much blending can lead to segregation. Such segregation effects are difficult to predict as they are a complex function of adhesive and cohesive interactions within the mixture. Here, the use of in-line Raman spectroscopy for noninvasive, real-time monitoring of the blending process is particularly valuable.

In a second experiment, it was found that the spectral region for fluticasone propionate and albuterol sulfate are unique, without any interference from the excipient α-lactose monohydrate. This allowed the detection of both molecules while in-line monitoring of the blending process with the Raman spectroscopic system. It was found that blends manufactured at three different concentrations of drug substances were homogenous and that principle component (PC1) scores were within 1 standard deviation. The peak area of drug substances was also linearly correlated with the concentration. Significantly, this further allows the use of in-line Raman spectroscopy for the quantitative determination of drug substances ($R^2 > 0.9$).

What is claimed is:

1. A dry powder for inhalation comprising fluticasone propionate, albuterol sulfate, and lactose monohydrate, wherein the albuterol sulfate is present in an amount greater than fluticasone propionate.

2. The dry powder as claimed in claim 1, wherein fluticasone propionate, albuterol sulfate and lactose monohydrate have distinguishable Raman peaks at 1672-1654 cm$^{-1}$, 790-775 cm$^{-1}$ and 1092-1082 cm$^{-1}$, respectively.

3. The dry powder as claimed in claim 1, wherein the lactose monohydrate is alpha-lactose monohydrate.

4. The dry powder as claimed in claim 1, wherein the fluticasone propionate and albuterol sulfate comprise micronized particles.

5. The dry powder as claimed in claim 4, wherein the fluticasone propionate and albuterol sulfate comprise micronized particles having an aerodynamic diameter of between about 0.1 microns to about 15 microns.

6. The dry powder as claimed in claim 4, wherein the micronized fluticasone propionate and micronized albuterol sulfate have a D90 of from 2.5 microns to 6 microns, and the alpha-lactose monohydrate has a D90 of from 100 microns to 300 microns.

7. The dry powder as claimed in claim 1, wherein the lactose monohydrate comprises a mixture of fine carrier particles and coarse carrier particles.

8. The dry powder as claimed in claim 7, wherein the fluticasone propionate is present in the powder in an amount of from about 0.1 wt. % to about 1 wt. %.

9. The dry powder as claimed in claim 7, wherein the fraction of fine carrier particles in coarse carrier particles is in the range of 0.1 wt. % to 20 wt. %.

10. The dry powder as claimed in claim 1, wherein the lactose monohydrate is present in an amount from about 80 to about 99.9 wt. %.

11. A method of treating lung diseases comprising administering a dry powder for inhalation comprising fluticasone propionate, albuterol sulfate, and lactose monohydrate, wherein the albuterol sulfate is present in an amount greater than fluticasone propionate.

12. The method of claim 11 wherein the lung disease is selected from the group consisting of: asthma, cystic fibrosis and COPD.

13. The method of claim 11 wherein the lung disease is Asthma.

14. The method as claimed in claim 11, wherein the fluticasone propionate and albuterol sulfate comprise micronized particles.

15. The method as claimed in claim 14, wherein the fluticasone propionate and albuterol sulfate comprise micronized particles having an aerodynamic diameter of between about 0.1 microns to about 15 microns.

16. The method as claimed in claim 14, wherein the micronized fluticasone propionate and micronized albuterol sulfate have a D90 of from 2.5 microns to 6 microns, and the alpha-lactose monohydrate has a D90 of from 100 microns to 300 microns.

17. The method as claimed in claim 11, wherein the fluticasone propionate is present in the powder in an amount of from about 0.1 wt. % to about 1 wt. %.

18. The method as claimed in claim 11, wherein the lactose monohydrate comprises a mixture of fine carrier particles and coarse carrier particles, whereby the fraction of fine carrier particles in coarse carrier particles is in the range of 0.1 wt. % to 20 wt. %.

19. The method as claimed in claim 11, wherein the lactose monohydrate is present in an amount from about 80 to about 99.9 wt. %.

20. A dry powder inhaler comprising a dry powder for inhalation comprising fluticasone propionate, albuterol sulfate, and lactose monohydrate, wherein the albuterol sulfate is present in an amount greater than fluticasone propionate.

21. The dry powder inhaler as claimed in claim 20, wherein the dry powder inhaler is selected from the group consisting of a single dose inhaler and a multidose inhaler.

22. The dry powder inhaler as claimed in claim 21, wherein the dry powder inhaler is a single dose inhaler.

23. The dry powder inhaler in claim 21 wherein the dry powder inhaler is selected from the group consisting of low-resistance devices (>90 L/min); (ii) medium-resistance devices (about 60 L/min); and (iii) high-resistance devices (about 30 L/min).

* * * * *